United States Patent [19]
Toso et al.

[11] Patent Number: 5,902,264
[45] Date of Patent: May 11, 1999

[54] ENDOSCOPIC SURGICAL INSTRUMENT FOR ASPIRATION AND IRRIGATION

[75] Inventors: Kenneth E. Toso, Wilton; Charles R. Sherts, Westport, both of Conn.

[73] Assignee: United States Surgical Corporation, Norwalk, Conn.

[21] Appl. No.: 08/845,313

[22] Filed: Apr. 25, 1997

Related U.S. Application Data

[60] Provisional application No. 60/016,157, Apr. 26, 1996, abandoned.

[51] Int. Cl.$^6$ ..................................................... A61M 1/00
[52] U.S. Cl. ............................... 604/27; 604/43; 604/118; 604/119; 600/130
[58] Field of Search .................................. 604/27, 19, 2, 604/26, 30, 33, 35, 48, 249, 902, 43, 110, 119; 600/156, 158, 159, 139, 104, 130; 606/115, 123

[56] References Cited

U.S. PATENT DOCUMENTS

| | | |
|---|---|---|
| Re. 31,272 | 6/1983 | Pevsner . |
| 1,740,174 | 12/1929 | Hevern . |
| 2,812,765 | 11/1957 | Tofflemire . |
| 3,208,145 | 9/1965 | Turner . |
| 3,527,203 | 9/1970 | Gravlee . |
| 3,735,751 | 5/1973 | Katz . |
| 3,850,175 | 11/1974 | Iglesias . |
| 3,929,126 | 12/1975 | Corsaut . |
| 3,994,297 | 11/1976 | Kopf . |
| 3,996,935 | 12/1976 | Banko . |
| 4,132,227 | 1/1979 | Ibe . |
| 4,149,315 | 4/1979 | Page, Jr. et al. . |
| 4,215,476 | 8/1980 | Armstrong . |
| 4,248,589 | 2/1981 | Lewis . |
| 4,320,761 | 3/1982 | Haddad . |
| 4,423,727 | 1/1984 | Widran et al. . |
| 4,465,470 | 8/1984 | Kelman . |
| 4,493,694 | 1/1985 | Wuchinich . |
| 4,517,962 | 5/1985 | Heckele . |
| 4,583,531 | 4/1986 | Mattchen . |
| 4,607,619 | 8/1986 | Seike et al. . |
| 4,643,711 | 2/1987 | Bates . |
| 4,655,743 | 4/1987 | Hyde . |
| 4,717,380 | 1/1988 | Baumgartner . |
| 4,723,550 | 2/1988 | Bales et al. . |
| 4,726,374 | 2/1988 | Bales et al. . |
| 4,744,360 | 5/1988 | Bath . |
| 4,747,820 | 5/1988 | Hornlein et al. . |
| 4,760,840 | 8/1988 | Fournier, Jr. et al. . |
| 4,776,840 | 10/1988 | Freitas et al. . |
| 4,790,812 | 12/1988 | Hawkins, Jr. et al. . |

(List continued on next page.)

FOREIGN PATENT DOCUMENTS

| | | |
|---|---|---|
| 0 199 848 | 5/1986 | European Pat. Off. . |
| 0 327 410 | 4/1989 | European Pat. Off. . |
| 0 411 170 | 2/1991 | European Pat. Off. . |
| 4 463 363 | 1/1992 | European Pat. Off. . |
| 234608 | 4/1986 | Germany . |
| 587044 | 4/1977 | Switzerland . |
| 2117245 | 10/1983 | United Kingdom . |
| 87/04610 | 8/1987 | WIPO . |
| 94/13355 | 6/1994 | WIPO . |

*Primary Examiner*—Wynn Wood Coggins
*Assistant Examiner*—N. Kent Gring

[57] ABSTRACT

An endoscopic surgical instrument for aspiration, irrigation, and blowing gas adjacent a surgical site is provided. The instrument includes a handle portion and a cannula member extending distally from the handle portion. First and second connection ports are supported by the handle and are in fluid communication with the cannula member. An insertion port is also supported by the handle portion and is preferably axially aligned with the cannula member. A blow tube is removably positioned within the cannula member via the insertion port. The first and second connection ports are adapted to communicate with a source of irrigation fluid and a vacuum source and the blow tube is adapted to be connected to a source of pressurized gas such that irrigation fluid, aspiration, and/or pressurized gas can be selectively provided via the cannula member at the surgical site.

20 Claims, 29 Drawing Sheets

U.S. PATENT DOCUMENTS

| | | |
|---|---|---|
| 4,846,790 | 7/1989 | Hornlein et al. . |
| 4,881,523 | 11/1989 | Heckele . |
| 4,886,491 | 12/1989 | Parisi et al. . |
| 4,896,678 | 1/1990 | Ogawa . |
| 4,904,246 | 2/1990 | Atkinson . |
| 4,921,476 | 5/1990 | Wuchinich . |
| 4,921,477 | 5/1990 | Davis . |
| 4,922,902 | 5/1990 | Wuchinich et al. . |
| 4,924,851 | 5/1990 | Ognier et al. . |
| 4,931,047 | 6/1990 | Broadwin et al. . |
| 4,947,827 | 8/1990 | Opie et al. . |
| 5,100,377 | 3/1992 | Freitas et al. . |
| 5,125,910 | 6/1992 | Freitas . |
| 5,186,714 | 2/1993 | Boudreault et al. . |
| 5,195,958 | 3/1993 | Phillips . |
| 5,197,948 | 3/1993 | Ghodsian . |
| 5,197,963 | 3/1993 | Parins . |
| 5,219,348 | 6/1993 | Buess et al. . |
| 5,230,704 | 7/1993 | Moberg et al. . |
| 5,244,459 | 9/1993 | Hill . |
| 5,273,524 | 12/1993 | Fox et al. . |
| 5,303,735 | 4/1994 | Cerola et al. . |
| 5,306,237 | 4/1994 | Clement et al. . |
| 5,310,406 | 5/1994 | Sharpe et al. . |
| 5,312,327 | 5/1994 | Bales et al. . |
| 5,312,332 | 5/1994 | Bales et al. . |
| 5,312,373 | 5/1994 | Freitas . |
| 5,322,503 | 6/1994 | Desai . |
| 5,324,254 | 6/1994 | Phillips . |
| 5,334,140 | 8/1994 | Phillips . |
| 5,348,555 | 9/1994 | Zinnanti . |
| 5,380,277 | 1/1995 | Phillips . |
| 5,447,494 | 9/1995 | Dorsey, III ................. 604/30 |
| 5,607,391 | 3/1997 | Klinger et al. ......... 604/35 X |
| 5,632,717 | 5/1997 | Yoon ....................... 600/106 |

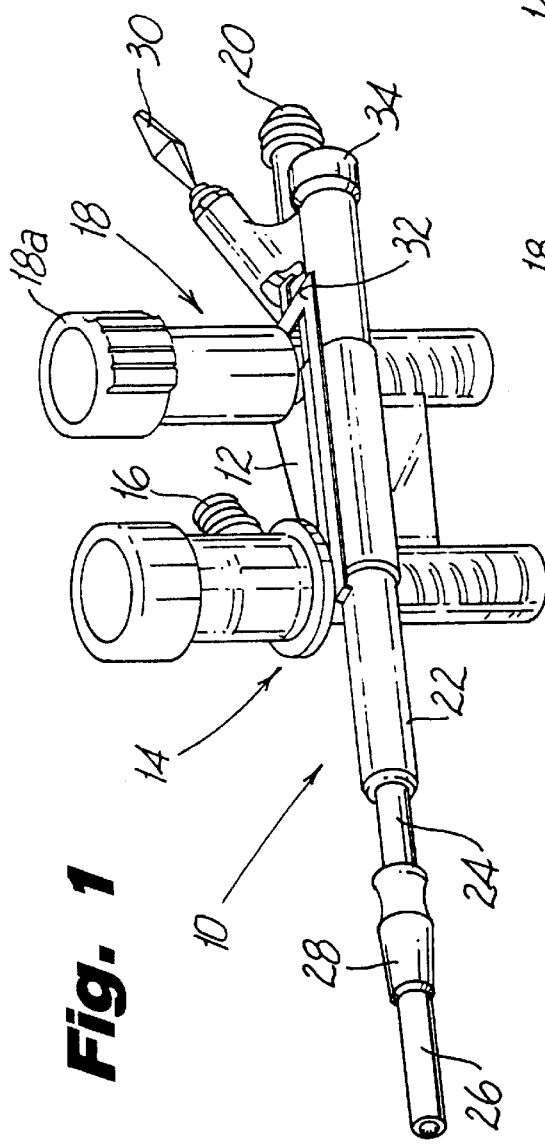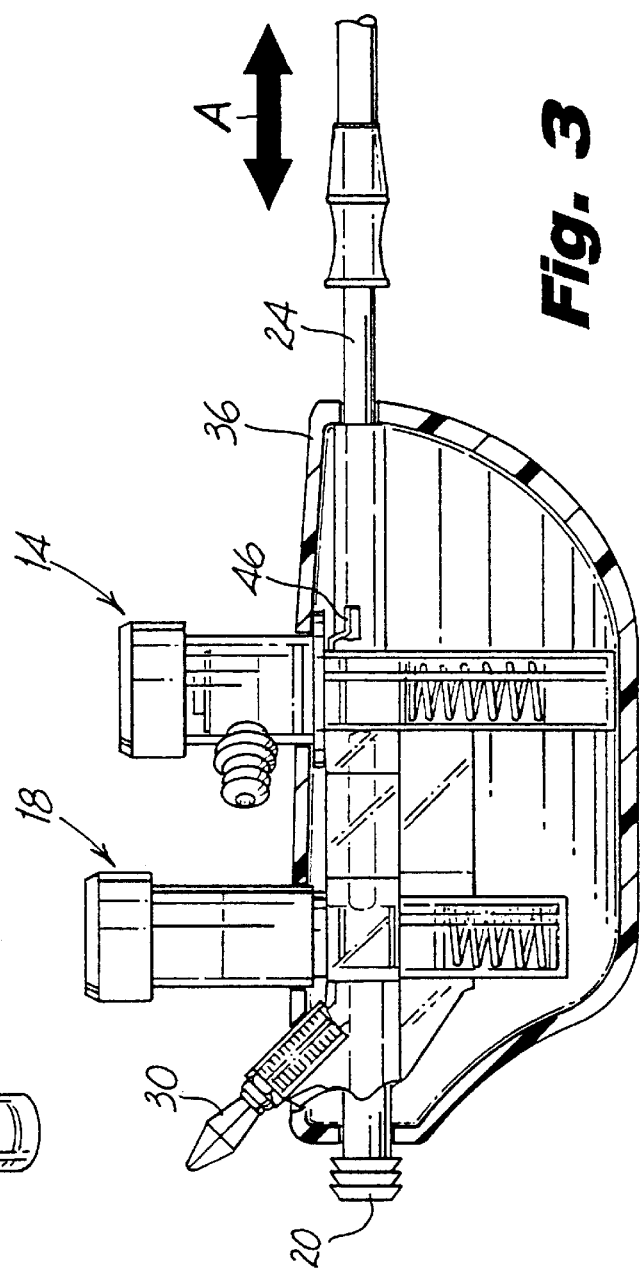

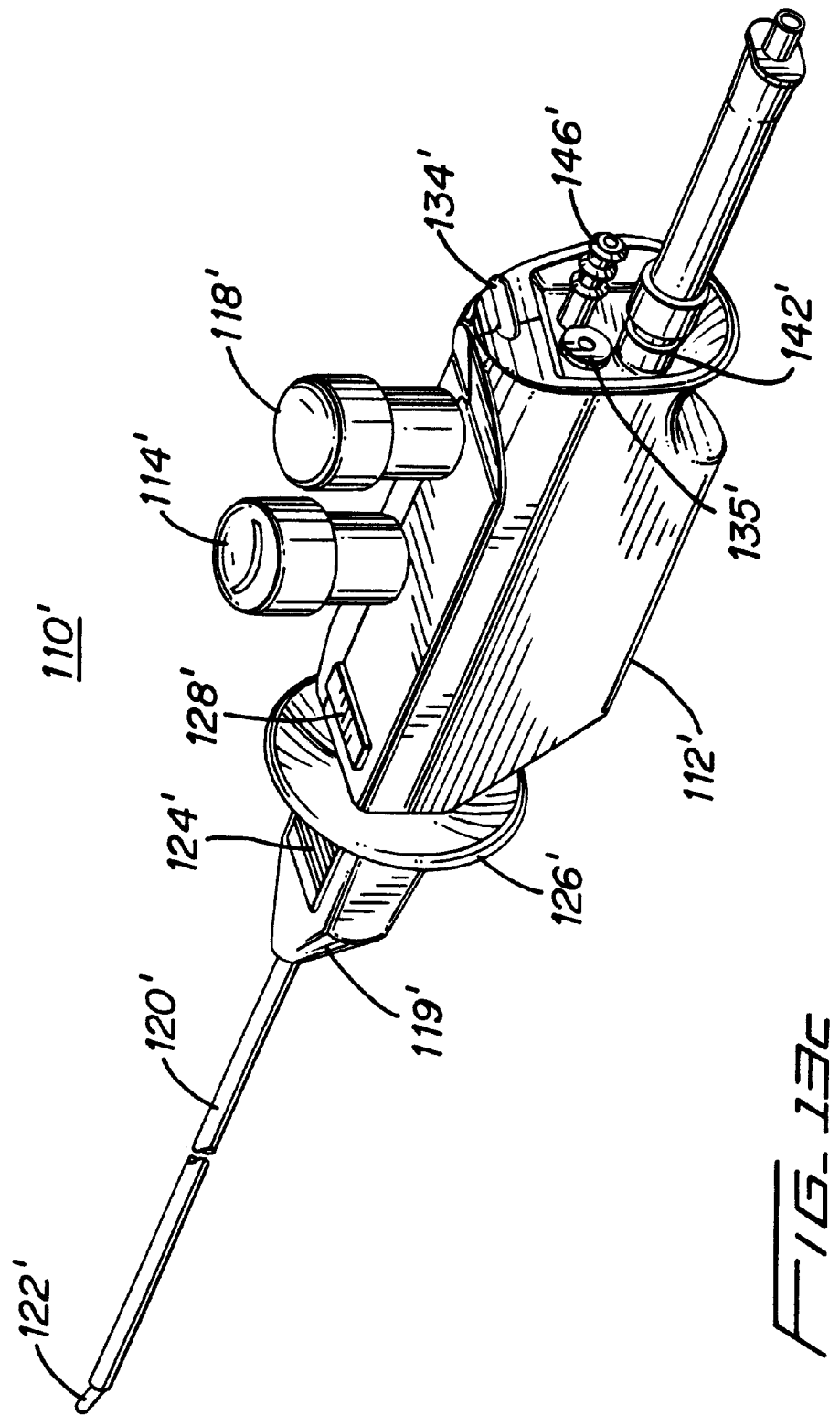

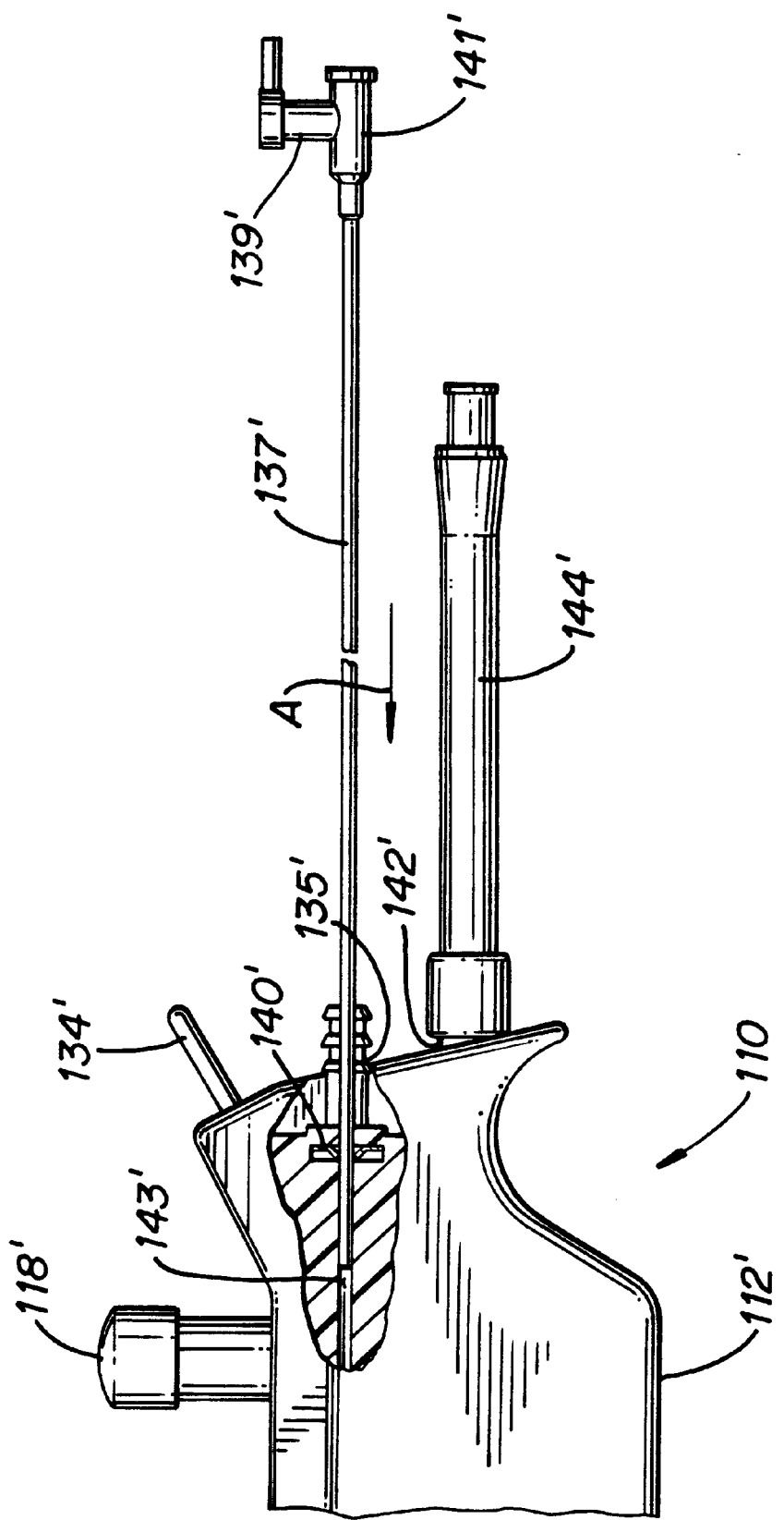

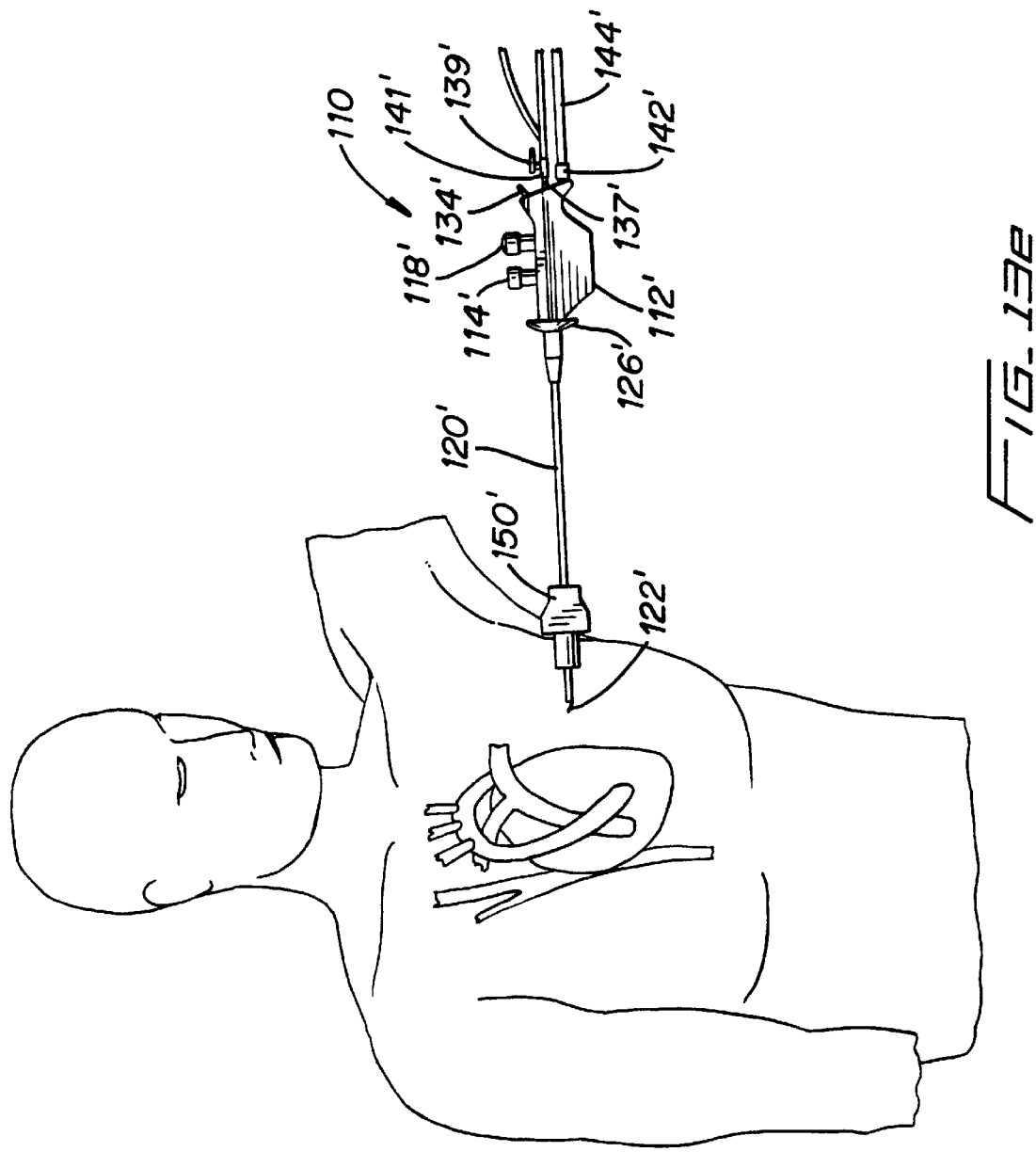

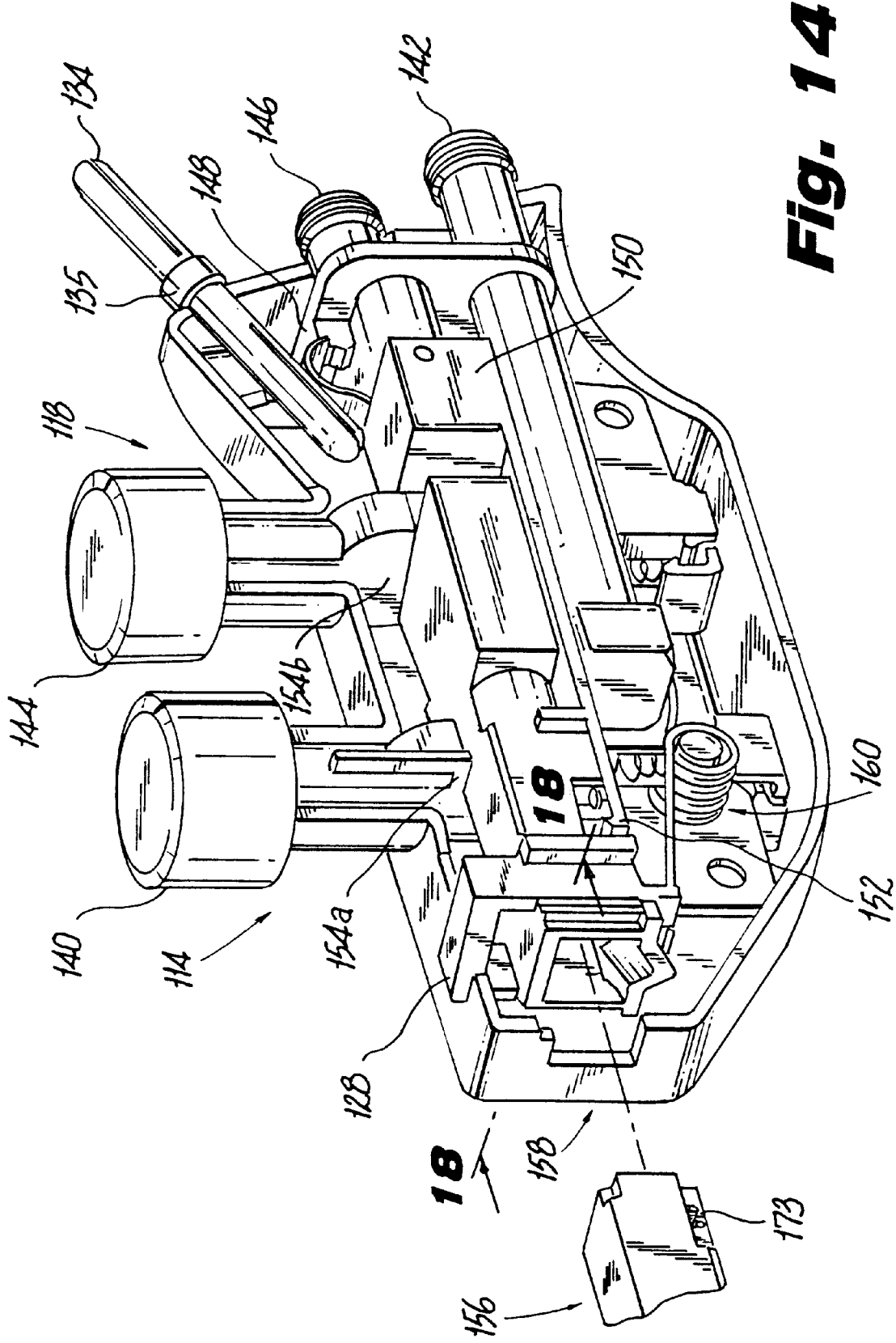

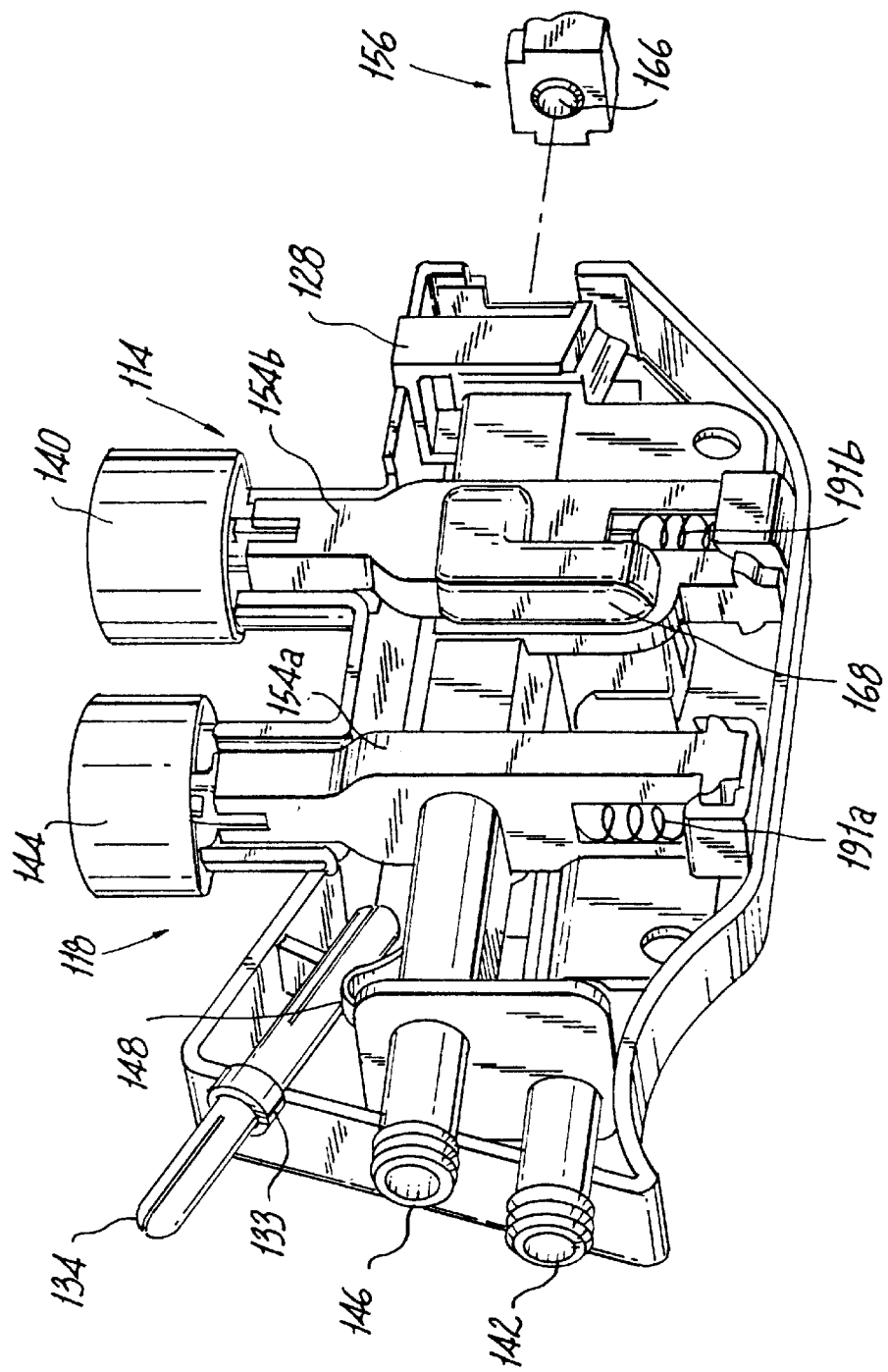

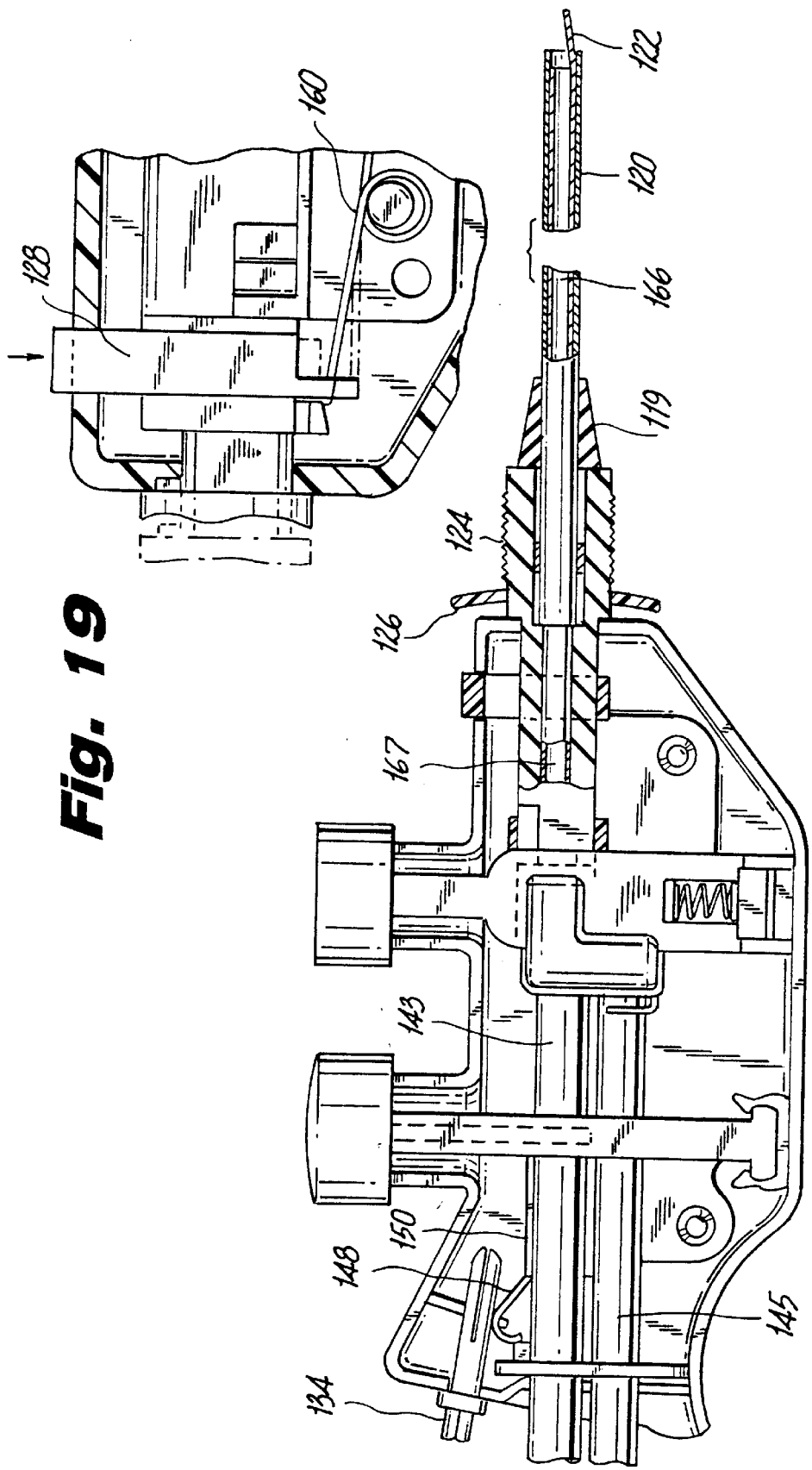

ENDOSCOPIC SURGICAL INSTRUMENT FOR ASPIRATION AND IRRIGATION

This application claims benefit of Provisional Application No. 60/016,157 Apr. 26, 1996 now abandoned.

BACKGROUND

1. Technical Field

The present application relates to endoscopic surgical instruments, and more particularly to endoscopic surgical instruments for aspirating, irrigating and blowing air at a surgical site.

2. Background of Related Art

Surgical devices for providing irrigation fluid and suction force to a surgical site to irrigate and evacuate the tissue in the area on which the surgical procedure is being performed are well known in the art. Several of these devices provide a handle member having a switching mechanism for turning on and off the flow of the fluid stream and suction force, and typically connect the suction source and the fluid source to an elongated flexible tubular member which is positioned adjacent the surgical site. In many instances, the tube or catheter includes a complex series of passages which provide a separate channel for the irrigation fluid and a separate channel for the suction force. Several devices include a pump source to provide the fluid under pressure; however, other devices provide a source of irrigation fluid which is operable under head pressure to gently wash the tissue. The prior art devices typically provide a large tube or catheter which enclose the several channels to deliver the fluid and provide the suction during oral surgery, or invasive surgery which allows for the positioning of the cumbersome tubing.

Several of the prior art devices provide numerous features including electrocautery, laser dissection, and viewing capabilities. Typically, the handle grip includes on/off switches in the form of trumpet valves which allow the surgeon to selectively choose the suction or irrigation feature. Many devices provide a pistol-type hand grip which allows the surgeon to operate the device with the thumb-actuated valves. Other devices provide tubular connections such as Luer-type connectors to couple the irrigation source or the suction source to the catheter or tube. Surgical devices for blowing air at a surgical site to improve visibility are also well known. Typically, these are separate devices.

With the recent developments in endoscopic and laparoscopic surgical procedures, it is necessary to provide a device in which many of the functions provided by the more complex and cumbersome prior art devices are included in a streamlined construction in which many of the features are provided in a single unit. In laparoscopic and endoscopic surgical procedures, a small incision or puncture is made in the patient's body to provide access for a tube or cannula device. The cannula is inserted into the patient's body through the provision of a trocar assembly which further includes an obturator for penetrating the body wall. After the obturator is removed, the cannula remains in place to maintain access to the surgical site. Once the cannula is in place, the surgical instrument may be inserted through the cannula to perform the procedure, while the surgical area is viewed through an endoscope or a miniature camera inserted through secondary cannulas to display the procedure on a video monitor.

The prior art devices are subject to several disadvantages when considered for use in laparoscopic or endoscopic surgical procedures. The primary focus behind such surgical procedures is that the surgery is minimally invasive to the patient's body, consequently reducing damage to surrounding tissue and organs and reducing the scarring resulting from the operation, which, as a result, greatly reduces recovery time for the patient. The prior art devices, which typically provide a plurality of channels in the tube or catheter portion to transport the suction force and irrigation fluid to the surgical site, are generally provided for invasive type surgery which allows the larger diameter catheters to be manually positioned adjacent the surgical objective through large incisions. Also, as discussed above, a separate device is required for blowing air at the surgical site.

Typical suction and irrigation devices having a hand grip in the shape of a pistol are disclosed in U.S. Pat. No. 4,149,315 to Page, Jr. et al. and U.S. Pat. No. 4,776,840 to Freitas et al. Page, Jr. et al. provides a dental suction/irrigation device which includes an elongated tube member which transports the suction force and the irrigation fluid to the tissue site. The elongated tubular member includes a pair of concentric tubes where the inner tube provides the irrigation fluid and the outer tube is provided for the suction. A pair of trumpet valves are provided to actuate the irrigation source and the aspiration source. Freitas et al. discloses a similar device but includes a complex internal manual pump to provide the irrigation fluid. A second flexible tube is provided for a vacuum source to evacuate fluid and gases from the surgical site.

U.S. Pat. No. 4,744,360 Bath provides a surgical device for removing cataract lenses which includes an optical fiber for laser surgery which is surrounded by an irrigation sleeve and a separate aspirator sleeve which provides fluid for irrigation and suction for evacuation, respectively, of the surgical site.

A Cabot Medical Corporation brochure (copyright 1990) discloses a suction/irrigation probe which includes a hydrodissection insert which has a rod which passes through the tube of the suction/irrigation probe to adjust the flow of the irrigation fluid.

U.S. Pat. No. 5,195,958 to Phillips illustrates a suction/irrigation/evacuation device for laparoscopic surgery. The hand piece has a variety of removably mounted attachments.

U.S. Pat. No. 5,310,406 to Sharpe et al. discloses an aspiration device for laparoscopic surgery having a large diameter tube with a proximal end. A tool access port concentric with the tube permits insertion of a grasping tool for holding a sponge at the distal end of the tube.

U.S. Pat. No. 5,312,332 to Bales et al. discloses an endoscopic electrosurgical suction-irrigation instrument which includes a valve through which an endoscopic tool may be inserted. The suction-irrigation instrument also includes a insulating sliding sleeve disposed about the metal cannula.

U.S. Pat. No. 5,322,503 to Desai discloses an endoscopic instrument for suction-irrigation which includes a port for the reception of instrumentation therethrough. The suction-irrigation instrument also includes electrocautery capabilities and a detachable probe which can be provided with a variety of working tips.

Other known devices include U.S. Pat. No. 4,921,476 and U.S. Pat. No. 4,493,694 to Wuchinich, and U.S. Pat. No. 3,527,203 to Gravlee, which include a tube having several channels for carrying the irrigation fluid separately from the suction device.

While these devices provide a way of communicating the fluid source to the surgical site, these prior art instruments typically operate only in a low pressure range, generally up to 25 psi. It has been found that in many surgical procedures, higher pressures are favorable to provide for hydrodissection, i.e. cutting through tissue by high pressure fluids. In addition, it is also necessary at times to provide greater aspiration forces to remove fluid, tissue, etc. A problem associated with the prior art devices is that many incorporate valve systems which are incapable of withstanding the higher static pressures. Furthermore, prior art devices generally provide for only a single irrigation or hydrodissection pressure for application at the surgical site. While it may be necessary to increase or lessen the pressure at the surgical site, many prior art devices do not provide this feature, and in these devices only the use of an external valve mechanism will accommodate such a feature.

In addition, while some prior art devices provide for other features such as electrocautery and laser cutting capabilities, in addition to suction and irrigation, these devices tend to have specific surgical applications, i.e. electrocautery only or laser only uses. In order to vary the procedure, the surgeon must switch instruments, thus requiring a number of instruments to be available in the operating room, e.g., a suction/irrigation device, an air blowing device, and an electrocautery device. The instruments also tend to be bulky, since separate, insulated lumens are often required in the cannula portion to permit electrocautery and laser procedures without injury to the patient or surgeon.

The novel endoscopic surgical device for suction, irrigation and blowing of tissue during a surgical procedure obviates the disadvantages encountered in the prior art and provides a compact instrument which includes many of the features necessary to perform the surgical procedure, and which is dimensioned to fit through a cannula for the performance of endoscopic or laparoscopic surgical procedures. The device also may accommodate higher pressures for the fluid source and the suction source by providing a novel valve mechanism having an improved valve, capable of withstanding static pressures of up to about 75 psi. The device of the present application includes a slidable sleeve to vary the suction forces gas, e.g. air and irrigation pressure as well as protect the tip of the instrument, particularly electrocautery tips. The working tip may be changed during the procedure, if desired, through the provision of interchangeable cannula tubes. In addition, the device described herein may be provided with an instrument insertion port for receiving a surgical instrument to be utilized with the suction and irrigation device during the surgical procedure.

SUMMARY

The device described herein provides a novel irrigation, aspiration and blowing instrument for performing endoscopic or laparoscopic surgical procedures. The device includes numerous features necessary for the performance of a surgical procedure such as dissection of tissue, or to provide suction, irrigation and blowing to a surgical site where the procedure is performed with additional instruments.

The suction and irrigation device described herein includes a subassembly having a connection port for a source of suction and a first valve mechanism to actuate the source of suction through the port, as well as a connection point for a source of irrigation and a second valve mechanism to actuate the source of irrigation through the port. A single lumen cannula is provided which communicates with the valve mechanisms for both the suction port and the irrigation port which transports the suction and the irrigation fluid to the surgical site, respectively. The device may further include an instrument insertion port configured to receive a surgical instrument, such as graspers and shears, in aligned communication with the single lumen cannula to locate the instrument through the cannula to the surgical site. Alternately, a blow tube may be positioned in the instrument insertion port to also provide blowing at the surgical site. The blow tube may be removably inserted into the insertion port or integrally formed with the body of the device. A valve mechanism is fastened to one end of the blow tube to control air flow at the surgical site. Furthermore, electrocautery may be provided for the performance of cauterization procedures at the surgical site.

A further feature of the device is the hydrodissection capability, in which the high pressure fluid may be directed to the tissue at high pressure to dissect the tissue. In this regard, a concentric outer sleeve member is provided along the length of the cannula which is longitudinally slidable to cover one or all of the apertures at the distal end of the cannula. This allows the surgeon to vary the pressure and provides a visual indication for adjusting the pressure at the distal end.

The device of the present application may also include a novel valve mechanism for accommodating fluid sources having higher static pressures than conventional instruments, up to about 75 psi. The valve mechanism preferably includes a pair of novel valves, each having a raised, ramped wall about its perimeter which increases the sealing force as the valves flex under higher pressures which allows for sealing under these higher pressure. The valves each include an aperture, for communicating either the suction or the fluid source with the cannula through a passageway in the body or handle of the instrument. The valves also include a membrane portion for occluding the passageway to prevent communication of either the suction or the fluid source with the cannula. Each valve preferably sits in an opening of a valve stem, the valve stems each being positioned in a valve body. Actuation of the valve stem causes movement of the corresponding valve between occlusion of the passageway and communication of the cannula with the source of suction or fluid. The membrane portion has its own raised ramped wall, which merges with the ramped wall about the perimeter of the valve. In a preferred embodiment, the valves have an oval shape, with the membrane portion having a ramped circular wall about it. The ramped cross-section of the two raised walls provides a frustoconical shape to the entire valve, and to the raised wall about the membrane portion. The raised wall about the perimeter of the valve merges with raised wall of the membrane portion at a tangential merger. At higher static pressures, the raised, ramped walls provide a greater surface pressure at the contact between the valves and the valve bodies, since the raised walls flex with the membrane portion to maintain the seal against the valve bodies.

The instrument of the present application also preferably includes electrocautery features. The slidable sleeve is preferably constructed of an electrically insulative material so as to insulate the cannula along its length, since the cannula is preferably constructed of a conductive material, such as metal. The sliding sleeve permits exposure and protection, depending on the positioning of the sleeve, of a tool member such as a dissector or spatula for performing electrocautery procedures. The spatula may be formed with smooth surfaces and rounded edges.

An additional feature of the present application is embodied in the interchangeable or replaceable cannulas, each of which may include a different working tip for performing a variety of surgical functions. Each cannula includes a connector at a proximal end for joining and detaching the cannula and the sliding sleeve to the instrument, while having a working tool at the distal end. Preferably, each cannula includes a slidable outer sleeve as described above, and also includes an electrical connection point at the proximal end for communicating an electrical charge along the length of the cannula, which is preferably conductive, to the working tool, if desired. It is also contemplated that at least one cannula does not have a working tool, and is not necessarily conductive, but instead is provided for suction and irrigation only. The detachable cannula and toll assembly described herein allows a surgeon to place the cannula assembly in a variety of positions for selectively positioning the working tool of the instrument with respect to the handle.

BRIEF DESCRIPTION OF TIE DRAWINGS

Various embodiments are described herein with reference to the drawings wherein:

FIG. 1 illustrates a perspective view of the subassembly of the endoscopic surgical instrument for aspiration and irrigation according to the present application;

FIG. 3 illustrates a side plan view in partial cross section of the embodiment of FIG. 2;

FIG. 13c illustrates a perspective view of another alternate embodiment of an endoscopic surgical instrument for aspirating, irrigating and blowing;

FIG. 13d illustrates a side partial cross-sectional view of the proximal end of the instrument of FIG. 13c with the blow tube partially inserted in the instrument bore;

FIG. 13e illustrates the instrument shown in FIG. 13c with the blow tube positioned in an insertion port adjacent the heart for bypass surgery;

FIG. 14 illustrates a front perspective view in partial cut-away of the handle of the instrument of FIG. 13a taken along lines 14—14;

FIG. 15 illustrates a rear perspective view in partial cut-away of the handle of the instrument of FIG. 13a taken along lines 14—14;

FIG. 16 illustrates a side cut-away plan view of the instrument of FIG. 13a taken along lines 16—16 with the slidable sleeve in a retracted position;

FIG. 18 illustrates a front cut-away plan view of the handle of the instrument showing the coupling mechanism for the detachable cannula of the instrument taken along lines 18—18 of FIG. 13a;

FIG. 19 illustrates a cross-sectional view of the handle of the instrument showing the coupling mechanism of the detachable cannula of the instrument taken along lines 19—19 of FIG. 18;

FIG. 20 illustrates a perspective view of the coupling end of the detachable cannula of FIG. 13a;

DETAILED DESCRIPTION OF THE PREFERRED EMBODIMENTS

Figure 2:
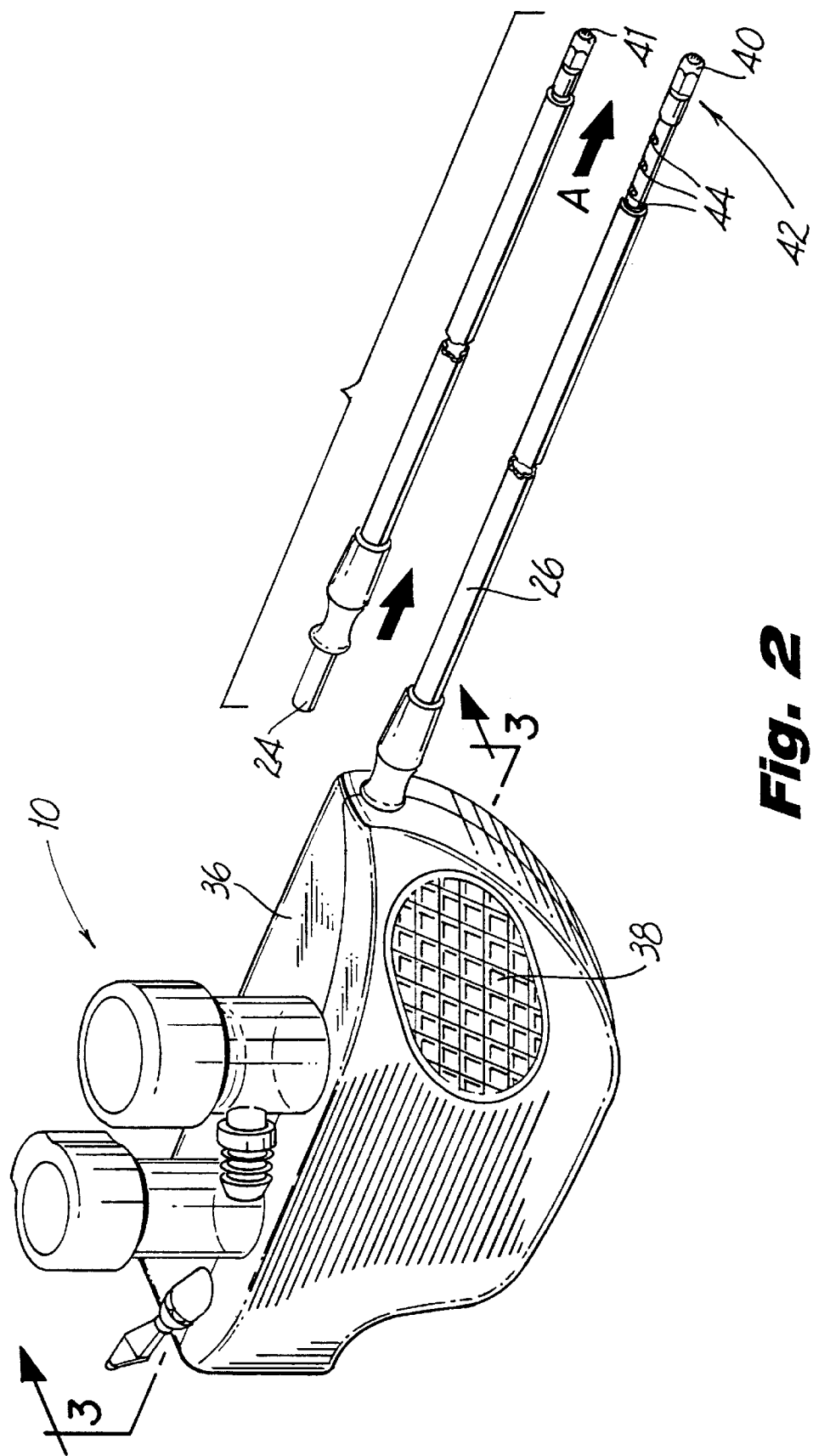
FIG. 2 illustrates a perspective view, including an external housing, according to a first embodiment.

Referring now in specific detail to the drawings, in which like reference numerals identify similar or identical elements throughout the several views, FIG. 1 shows the endoscopic surgical instrument for aspiration and irrigation according to the present application. Instrument 10 includes a body portion 12 to which at least a pair of valve members 14 and 18 are attached. Preferably, at least one valve member, namely valve member 14, includes a rotatable connection port 16 for coupling a source of irrigation or a source of suction thereto. Valve member 18 may include a rotatable connection port; however, in a preferred embodiment valve member 18 includes a rotatably lockable actuator 18a for maintaining a source of constant irrigation or suction. Connection port 20 is controlled by valve member 18.

Body portion 12 includes a mixing chamber which communicates with both connection port 16 and connection port 20 through valve member 14 and 18, respectively. Body portion 12 extends into coupling member 22 which couples the mixing chamber with a single lumen cannula 24. Single lumen cannula 24 provides a way of transporting the irrigation fluid or the suction force from their respective sources to the surgical site. Single lumen cannula 24 simplifies the construction of device 10 and significantly reduces cost in that a single tubular member having a reduced diameter single channel therethrough is utilized to carry both the suction and irrigation fluid to the surgical site.

Preferably, single lumen cannula 24 is enclosed within outer sleeve member 26 which concentrically surrounds and contacts single lumen cannula 24 along its length and is slidable in a longitudinal direction by collar 28. The purpose of the slidable outer sleeve will be discussed below.

Device 10 may further include a bayonet-type adapter 30 for providing electrocautery capabilities to device 10. Bayonet adapter 30 is in electrical contact with single lumen cannula 24 through the provision of bus bar 32. Bayonet adapter 30 provides for cauterization at the surgical site and for electrodissection of tissue. Device 10 may further include instrument insertion port 34 configured to receive a surgical instrument, such as endoscopic shears or graspers, and in direct axial alignment with single lumen cannula 24.

FIG. 2 illustrates the device of FIG. 1 enclosed in a working housing 36 which provides for gripping and handling of device 10. Housing 36 may be provided with scored portion 38 in one or several locations to facilitate gripping. As is seen in FIG. 2, single lumen cannula 24 is enclosed by outer sleeve member 26 which is slidable between a proximal position whereby apertures 44 are exposed at the distal end 42, to a distal position where outer sleeve 26 covers apertures 44. A hydrodissection tip 40 is shown as connected to the distal end 42 of single lumen cannula 24. In use, device 10 may be utilized for hydrodissection purposes. In such a case, a high pressure irrigation fluid source is utilized and connected, preferably to either of connection port 16 or connection port 20. As the irrigation fluid exits the aperture 41 at the end of hydrodissection tip 40, the pressure at which the fluid exits may be regulated and varied by sliding outer sleeve 26 in the direction of arrow A to cover one or more of apertures 44. Covering apertures 44 will increase the pressure of the fluid exiting tip 40 to provide for greater or less pressure of the irrigation and dissection fluid.

Preferably, outer sleeve 26 is constructed of an electrical insulating material, such as plastic, or may be provided with an electrically insulating shrink tubing, so that when device 10 is used for electrocautery purposes, the risk of shock is mitigated. FIG. 3 shows the electrical connection of bayonet adapter 30 with single lumen cannula 24 at connection point 46.

Figure 4:
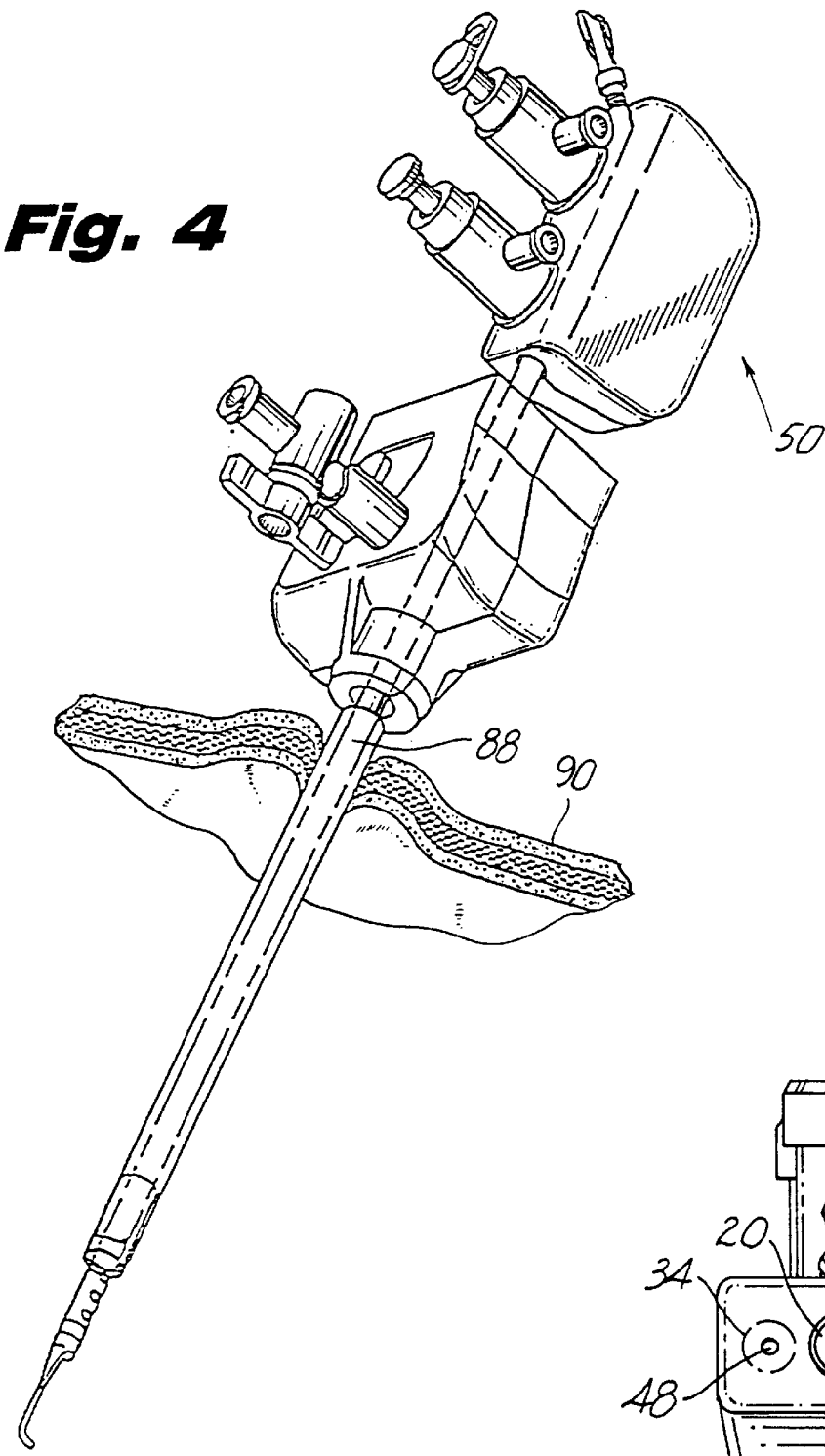
FIG. 4 illustrates a perspective view of an embodiment of the endoscopic surgical instrument for aspiration and irrigation according to the present application in use during a surgical procedure.

FIG. 4 illustrates an exemplary suction and irrigation device 50 in use at a surgical site. The body wall 90 of the patient is penetrated by a trocar assembly, the cannula 88 of which remains in place after the pointed obturator has been removed. Instrument 50 is inserted to the surgical site through cannula 88 as shown to perform the surgical procedure.

Figure 5:
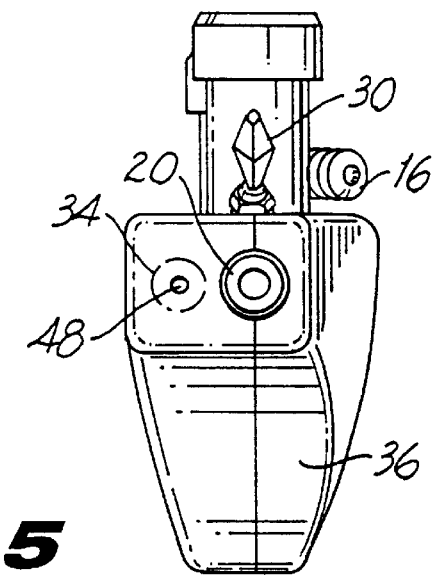
FIG. 5 illustrates a rear plan view of the device of FIG. 2.

FIG. 5 illustrates a rear view of the device of FIG. 2 which illustrates connection port 20 as being in axial alignment with valve members 14 and 18, while instrument insertion port 34 is in direct axial alignment with single lumen cannula 24.

Figure 6:
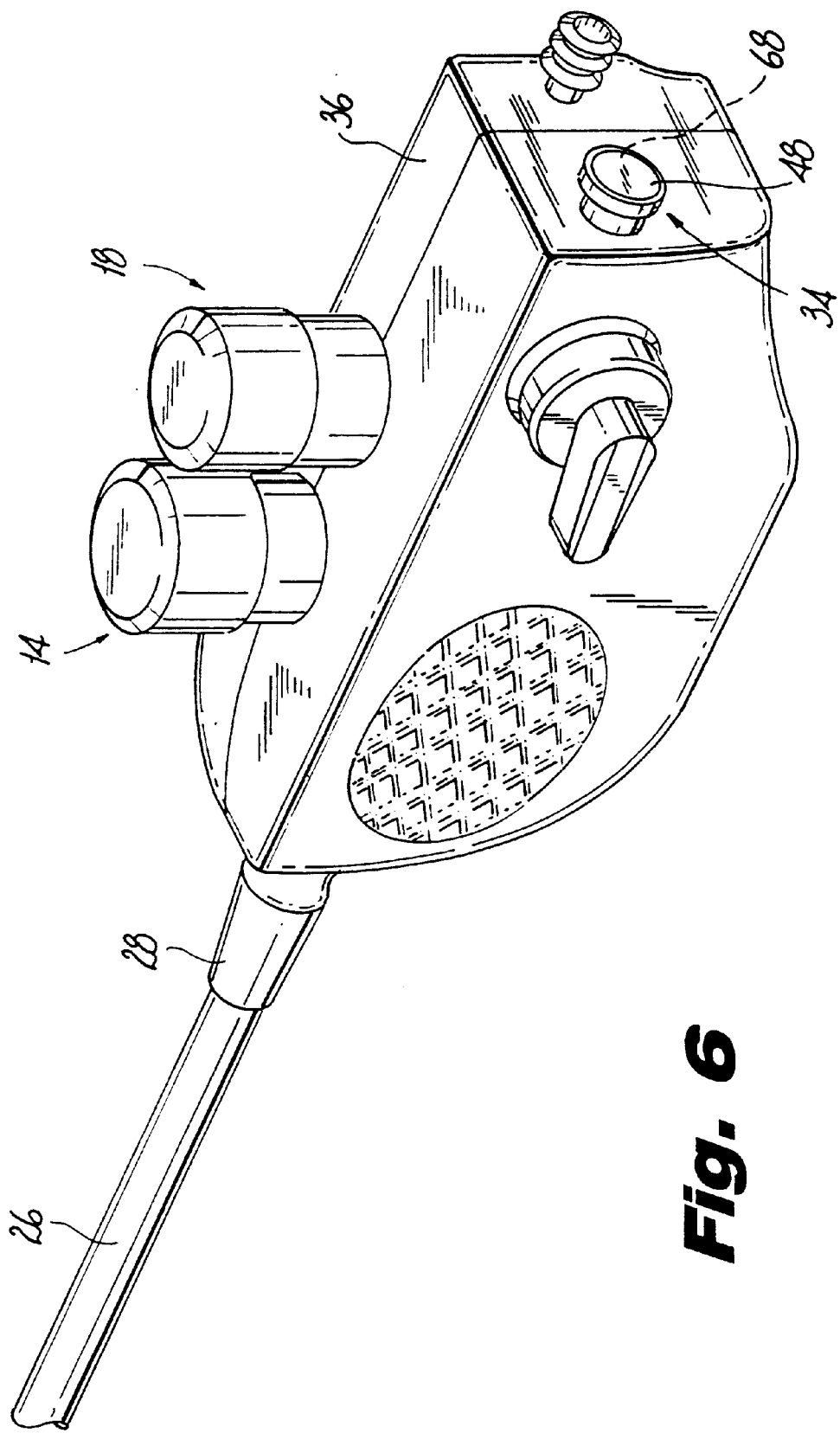
FIG. 6 is a perspective view of the aspiration-irrigation device of the first embodiment including an instrument insertion port having a sealing member of a first embodiment and locking system.
Figure 6A:
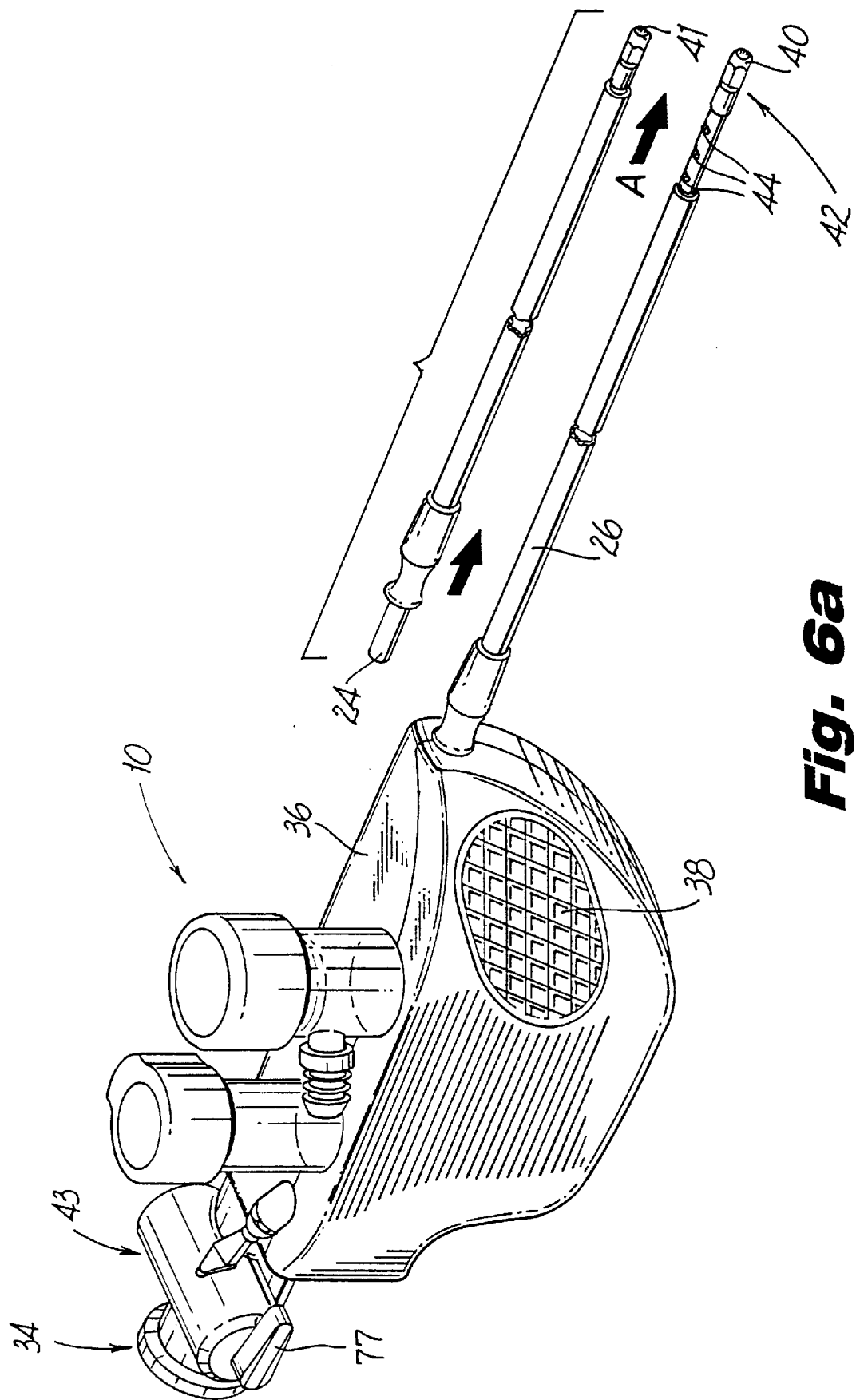
FIG. 6a is a perspective view of the aspiration-irrigation device of the first embodiment including an instrument insertion port having a sealing member of a second embodiment.
Figure 7:
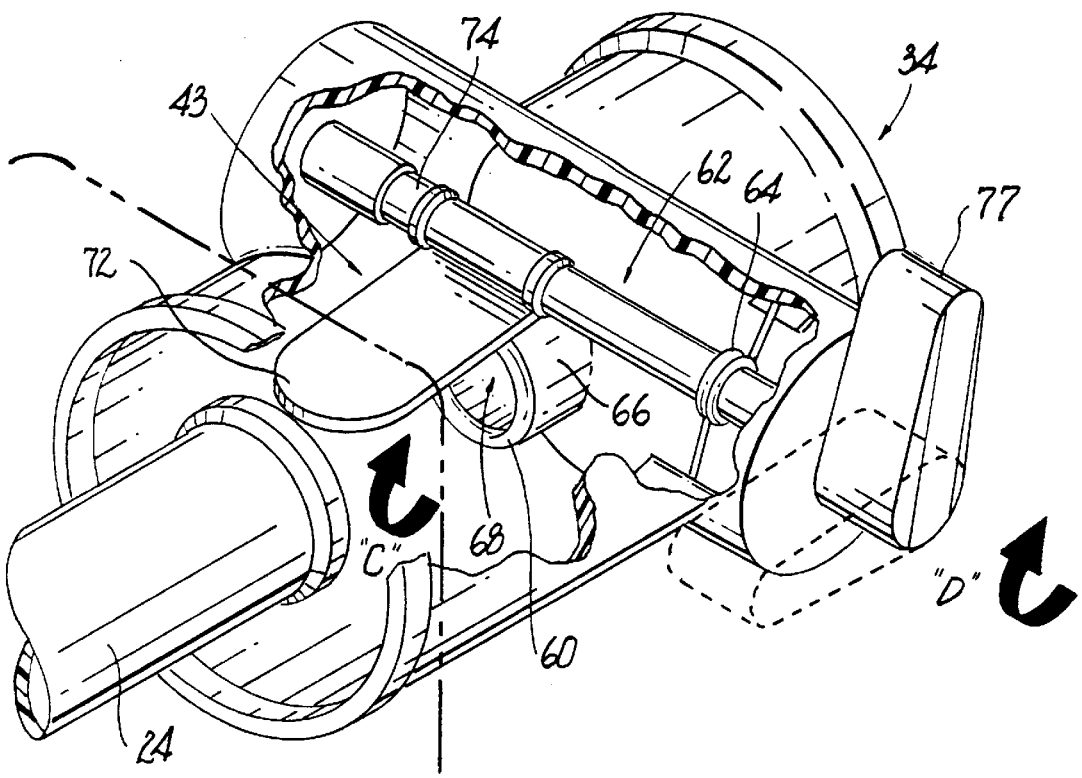
FIGS. 7, 8 and 9 illustrate an exemplary flapper valve assembly for the instrument insertion port.
Figure 10:
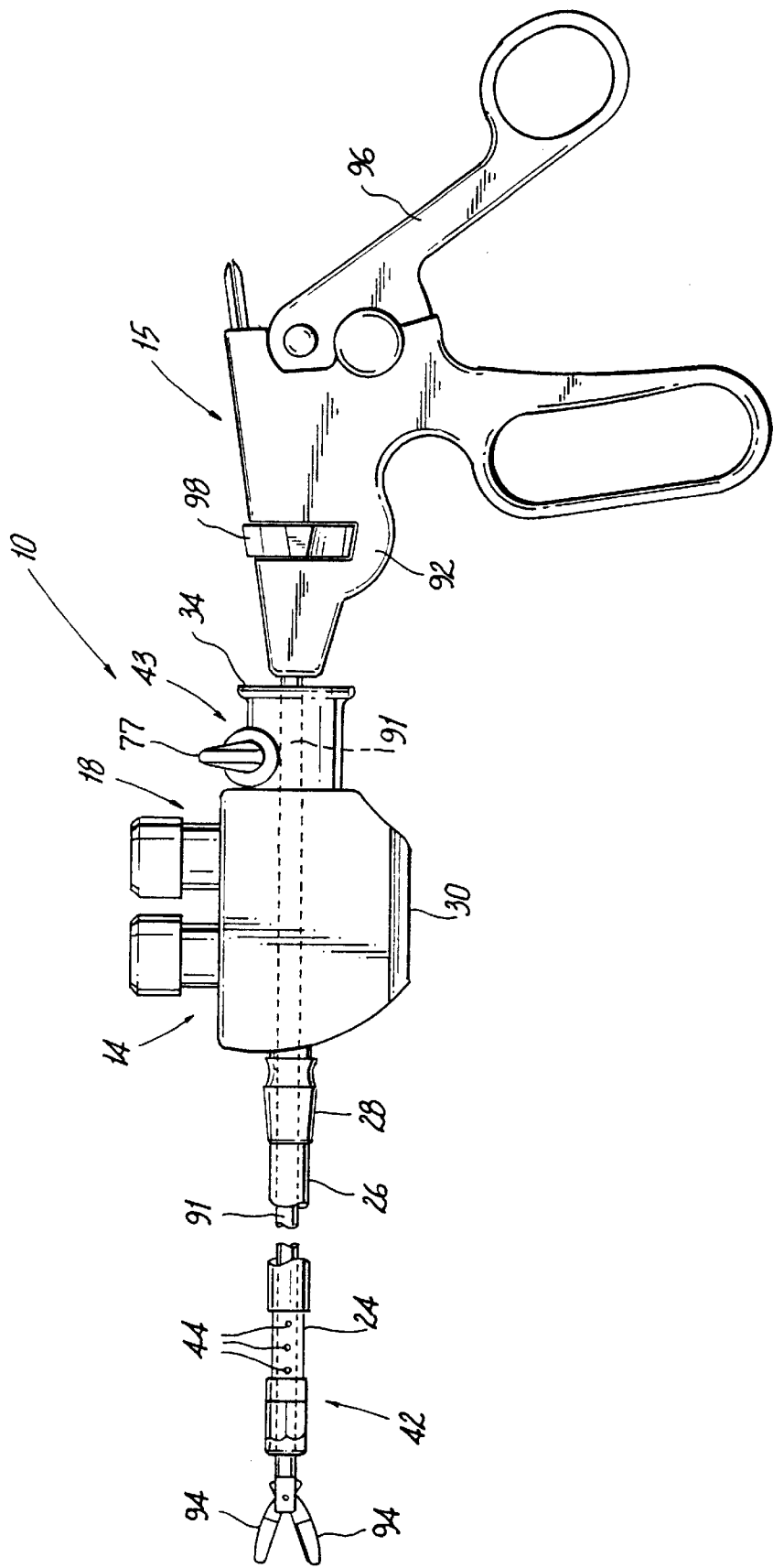
FIG. 10 is a side elevational view illustrating an exemplary aspiration-irrigation assembly including the flapper valve of FIGS. 7, 8, and 9 and having an endoscopic surgical tool inserted therein.

Instrument insertion port 34 permits insertion of an endoscopic surgical instrument to the surgical site within the body cavity. Instrument insertion port 34 may be monolithically formed within housing 36, as shown in FIGS. 5 and 6, or may be connected to housing 36, as shown in FIGS. 6a and 10. To maintain proper insufflation of body cavities and to prevent fluid from passing through cannula 24 and out of housing 36 a sealing system or member is provided and described hereinbelow.

Figure 12:
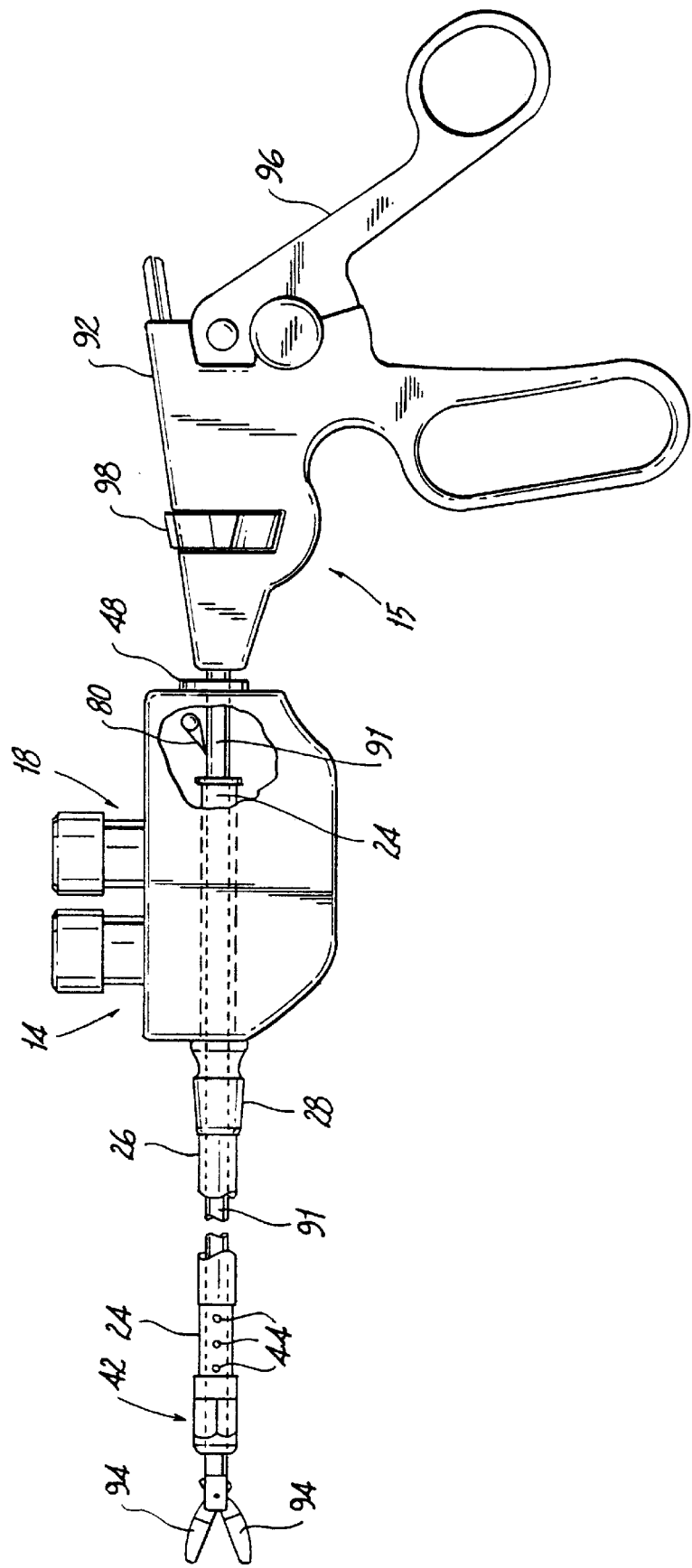
FIG. 12 is a side elevational view in partial cut-away, similar to FIG. 9, illustrating the locking system engaged with the tool portion.

In one embodiment shown in FIGS. 5,6 and 12, the sealing system is a self-sealing elastomeric member 48 which expands to allow insertion of instrument 15 (FIG. 12) and provides a sealed engagement therewith. Elastomeric member 48 retracts to seal opening 68, defined by elastomeric member 48, when the endoscopic surgical instrument is removed. To further provide a fluid tight seal so as to maintain insufflation and to prevent fluid from exiting the aspiration-irrigation device 10, a self-sealing elastomeric member similar to sealing member 48 may be positioned at the proximal end of single lumen cannula 24.

Figure 8:
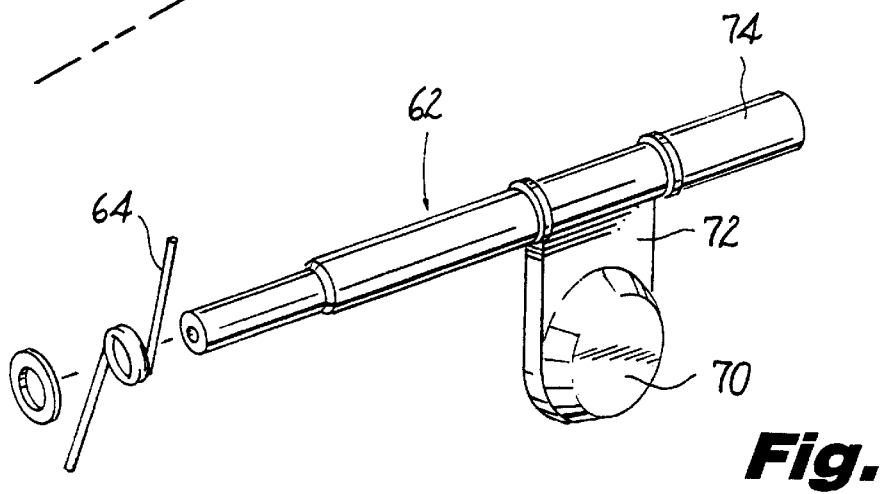
Figure 9:
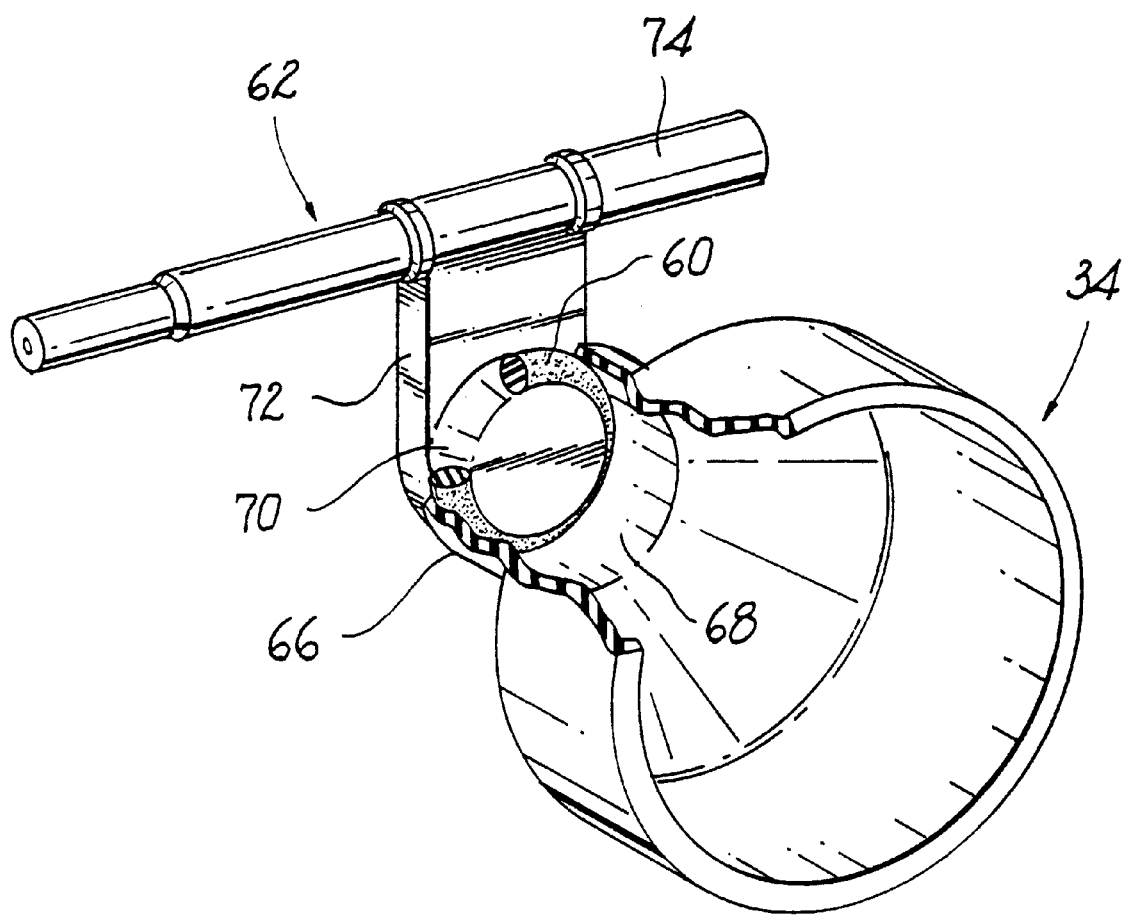

In an alternate embodiment of device 10 shown in FIGS. 6a–10, the sealing system is a flapper valve assembly 43. The flapper valve assembly includes valve seat 60, valve arm assembly 62 and biasing spring 64 which are positioned between insertion port 34 and the proximal end portion of cannula 24. Preferably, the valve seat 60 is a tubular member or ring extending from flange 66 of insertion port 34 which defines opening 68 which is in aligned communication with the opening of single lumen cannula 24. Valve plug 70, shown in FIG. 8, is secured to valve plate 72 and the combination is secured to post 74 to form valve arm assembly 62. Valve arm assembly 62 provides a sealed engagement with opening 68 in valve seat 60.

For the embodiment of FIGS. 6a–10, valve arm assembly 62 is pivotally mounted within connector port housing 76 via post 74. Biasing spring 64 is positioned on post 74 and in engagement with an interior wall portion of housing 76 to bias valve plug 70 toward a position of engagement with valve seat 60 to effect a gas tight and fluid tight seal in absence of a surgical instrument disposed therethrough. Thus, when endoscopic portion 91 of instrument 15, shown in FIG. 10, is inserted into connector port 34 and cannula 24, valve plate 72 is pivoted in the direction of arrow "C", shown in FIG. 7. Valve seat 60 engages the outer wall of endoscopic portion 91 and maintains proper insufflation of the body cavity, as well as prevents fluid from passing therethrough. Valve plate 72 may also be pivoted manually by rotating lever arm 77 in the direction of arrow "D".

Referring now to FIG. 10, the distal end portion of endoscopic section 90 includes actuable jaws 94 which are interconnected with pivoting handle 96 associated with handle member 92. Jaws 94 are responsive to the pivotal movement of the pivoting handle 96 so as to open and close the jaws. Thumb wheel 98 is rotatably mounted within handle member 92 and is operatively connected to a proximal end portion of endoscopic portion 91 to facilitate rotational movement of the endoscopic portion 91 and jaws 94. A more detailed description of the structure and operation of an exemplary endoscopic surgical instrument is described in commonly assigned, U.S. patent application Ser. No. 08/253,826 filed Jun. 3, 1994 now U.S. Pat. No. 5,522,830 which is incorporated herein by reference.

Figure 11:
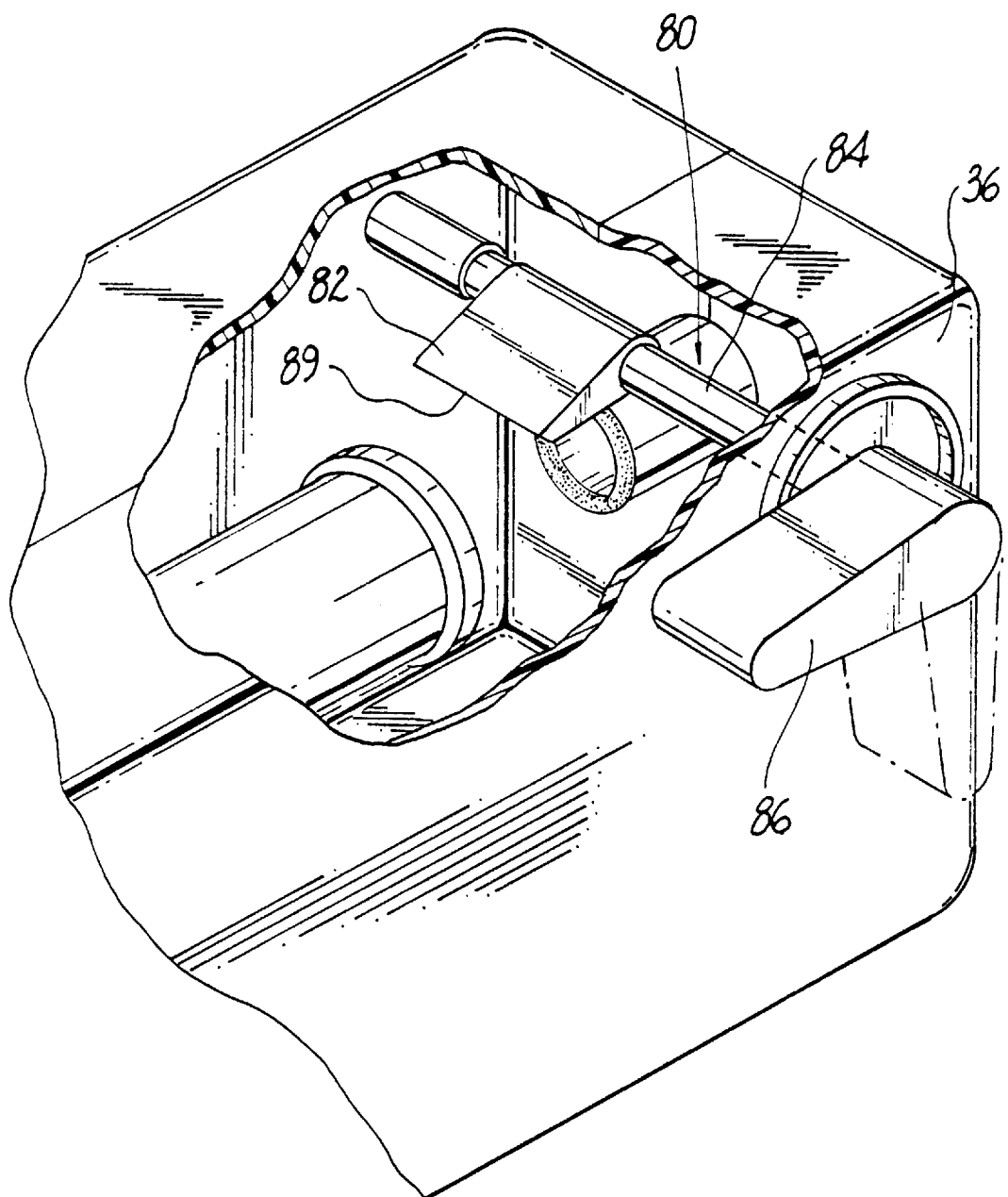
FIG. 11 is a partial perspective view of a portion of the interior of the irrigation-aspiration housing, illustrating an instrument locking system.

Referring now to FIGS. 11 and 12, an instrument locking member 80 is provided to maintain surgical instrument 15 in a fixed relationship with respect to cannula 24 and insertion port 34. Instrument locking member 80, shown in detail in FIG. 11, includes camming flap 82 secured to post 84, and lever arm 86 secured to a portion of post 84 extending from housing 36. To maintain the positioning of instrument 15 with respect to cannula 24, a surgeon rotates lever arm 86 so that the camming surface 89 of flap 82 engages endoscopic portion 91 of instrument 15, as shown in FIG. 12. Alternatively, the instrument locking member may be a thumb screw positioned on housing 36 which when tightened engages endoscopic section 91 of surgical instrument 15 so as to maintain the instrument 15 in a fixed relationship with cannula 24 and insertion port 34. Although shown in conjunction with elastomeric self-sealing member 48, the instrument locking member 80 may also be used in conjunction with flapper valve assembly 43.

Figure 13A:
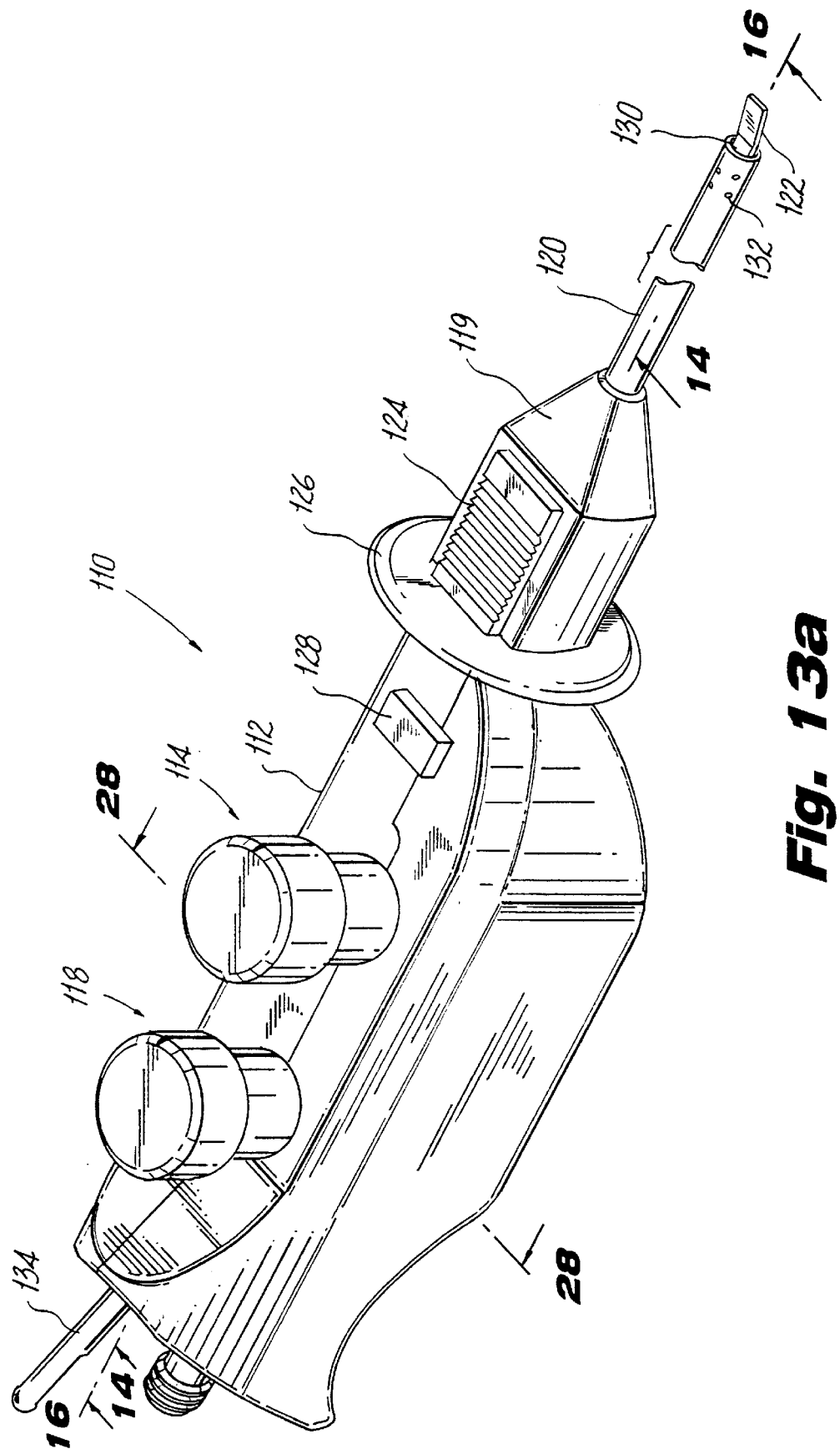
FIG. 13a illustrates a perspective view of an alternate embodiment of the endoscopic surgical instrument for aspiration and irrigation of the present application.

An alternate embodiment of the surgical instrument for aspiration and irrigation is illustrated in FIG. 13a. The instrument of FIG. 13a is similar to the instrument shown in FIG. 1 with the added provision of a removable cannula assembly which allows the user to utilize a plurality of cannula assemblies, each preferably having a different tool mechanism at its distal end. As seen in FIG. 13a, instrument 110 includes a handle portion 112 which encloses valve mechanisms 114 and 118. Extending from the handle portion 112 is a detachable and replaceable cannula assembly 116, which will be described in greater detail below. Cannula assembly 116 includes a body portion 119 and preferably further includes a cannula sleeve 120 which is slidably positioned over cannula tube 130. To facilitate movement of cannula sleeve 120 over cannula tube 130, a collar 126 is provided which permits the surgeon to slide cannula sleeve 120 over tool member 122 with one hand, and further provides a shield for the surgeon's hand at the distal end of the handle 112. A grip portion 124 is also provided at the proximal end of cannula assembly 116 to facilitate handling and insertion of the cannula assembly. Sliding sleeve 120 preferably also includes a plurality of apertures 132 whose function will be described below.

Referring to FIG. 13c, an alternate embodiment of the instrument is shown which incorporates blowing. More specifically instrument 110' includes instrument insertion port 135', connection port 142', and connection port 146' which extend from the proximal end of the instrument 110'. Connection port 142' is controlled by valve mechanism 114' and is adapted to communicate with a source of irrigation. Connection port 146' is controlled by valve mechanism 118' and is adapted to communicate with a source of suction. In this embodiment, the instrument insertion port 135' is configured to receive a surgical blow tube 137' (FIG. 13d). Insertion port 135' communicates with bore 143' which is axially aligned with the opening in cannula tube 130'.

FIG. 13d illustrates blow tube 137' positioned within the instrument insertion port 135'. The blow tube 137' is slid into insertion port 135' in the direction indicated by arrow "A" through the bore 143' of handle 112' and through the cannula tube (not shown) positioned within sleeve 120' to a position adjacent the distal end of the cannula tube. A stopcock or valve mechanism 139' and an adapter 141' are fastened to the proximal end of the blow tube 137'. The adapter 141' is configured to engage a source of pressurized gas, e.g., $O_2$, $CO_2$, such that the instrument 110' is capable of providin blowing in addition to irrigation and suction. An elastomeric seal 140' is positioned adjacent the insertion port 135' to sealingly engage the proximal end of the blow tube 137'. Alternately, the blow tube 137' may be integrally formed with the instrument 110' and thus may not require a seal. An extension adapter 144' may be fastened to connection port 142' to facilitate connection of connection port 142 with the source of irrigation.

Tool 122' is shown in the form of a spatula tip with smooth surfaces and rounded edges to dissect, manipulate or cauterize. Optionally the tip can be coated with Teflon.

The instrument 110', including blow tube 137', is particularly suited for use while performing minimally invasive heart bypass surgery. As illustrated in FIG. 13e, during a bypass procedure the sleeve 120' is inserted through the chest wall via a cannula 150' into the thoracic cavity between two adjacent ribs such that the distal ends of sleeve 120' and cannula 130' (not shown) are positioned adjacent the surgical site. In this position, any one of the valve mechanisms 114', 118' and 141' may be actuated to provide suction, irrigation or blowing at the surgical site. For example, valve mechanism 118' may be actuated to provide suction at the surgical site to remove blood or tissue from the thoracic cavity or valve mechanism 141' may be actuated to disperse the blood to improve visibility at the surgical site.

Figure 18:
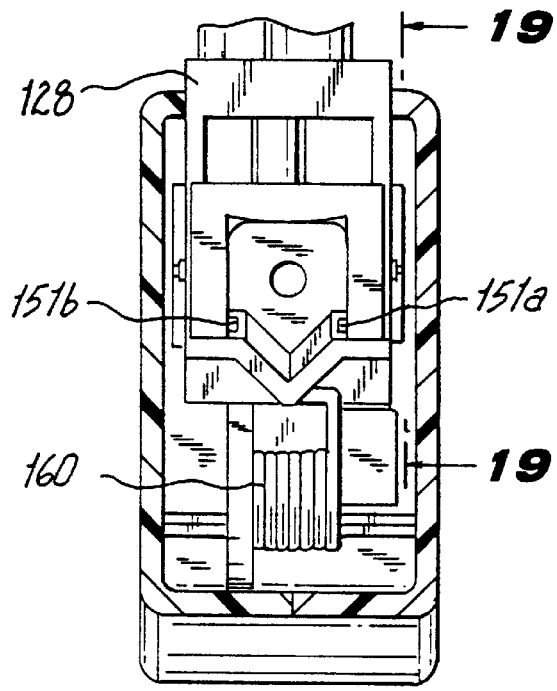

FIGS. 14 and 15 illustrate the internal portion of the handle 112 with opposite sides of handle portion 112 removed. Bayonet adapter 134 is preferably a male connector which is removably secured through an aperture 133 in handle portion 112 to provide an electrical connection between the instrument and an electrical power source having a female connector (not shown). Bayonet adapter 134 can be removed in order to allow instrument 110 to accept a male connector from the electrical power source through aperture 133. A collar 135 is provided to prevent over insertion of bayonet adapter 134 into the housing. An electrical leaf spring 148 located in handle portion 112 continues the electrical path from the bayonet adapter 134 to bus bar assembly 150. Bus bar assembly 150 carries the electrical connection to the detachable cannula assembly 116 via two electrical leaf springs 151a and 151b (FIG. 18) which are provided in cannula port 158 to complete the connection to electrical contacts 173 and 174 (FIGS. 14 and 20) on cannula coupling member 156. Electrical contacts 173 and 174 are electrically connected to electrically conductive cannula tube 130 to provide electrocautery capabilities to tool member 122 at the distal end of the cannula assembly 116.

Figure 13B:
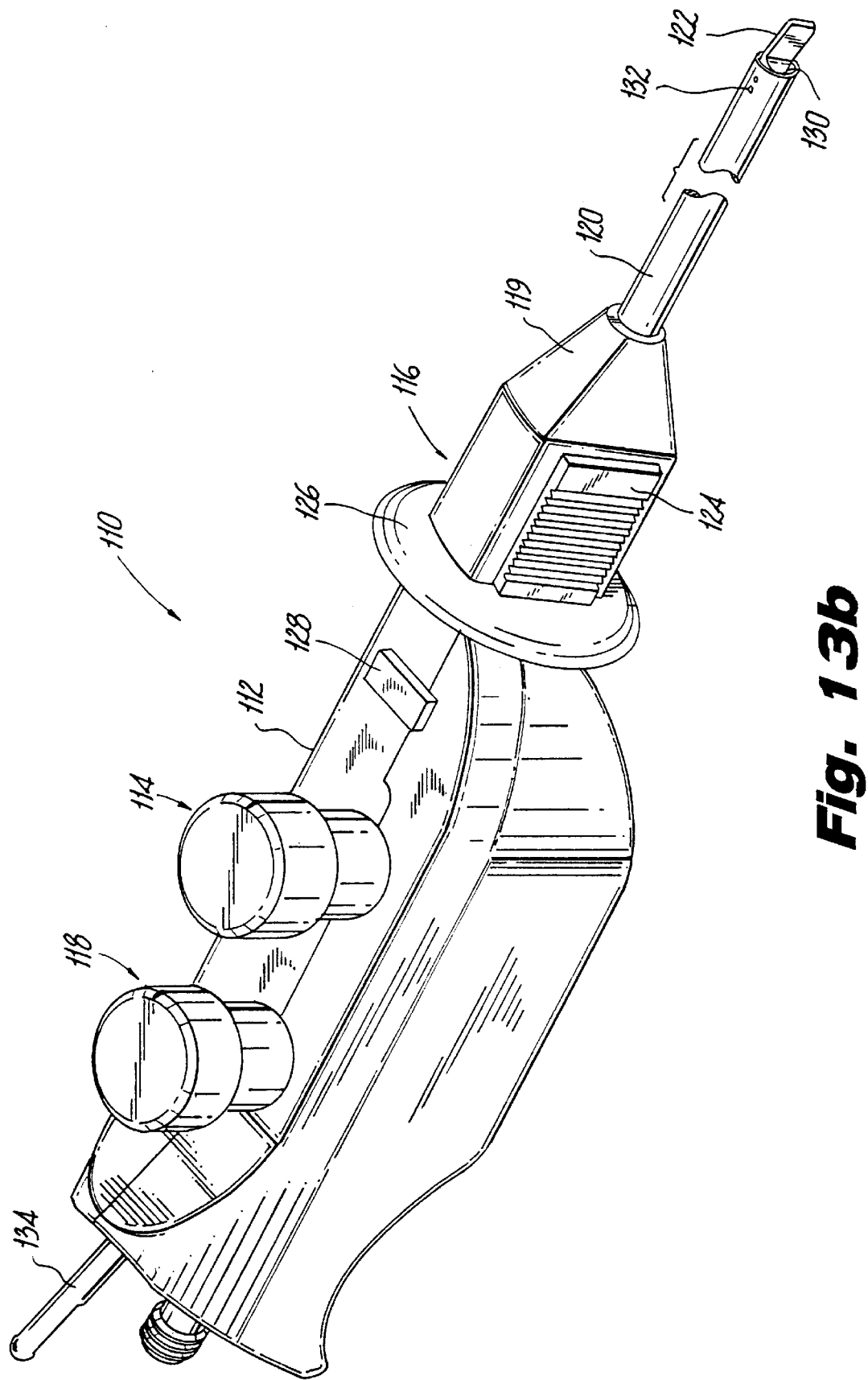
FIG. 13b illustrates a perspective view of the instrument of FIG. 13a with the detachable cannula and tool mechanism rotated 90°.
Figure 17:
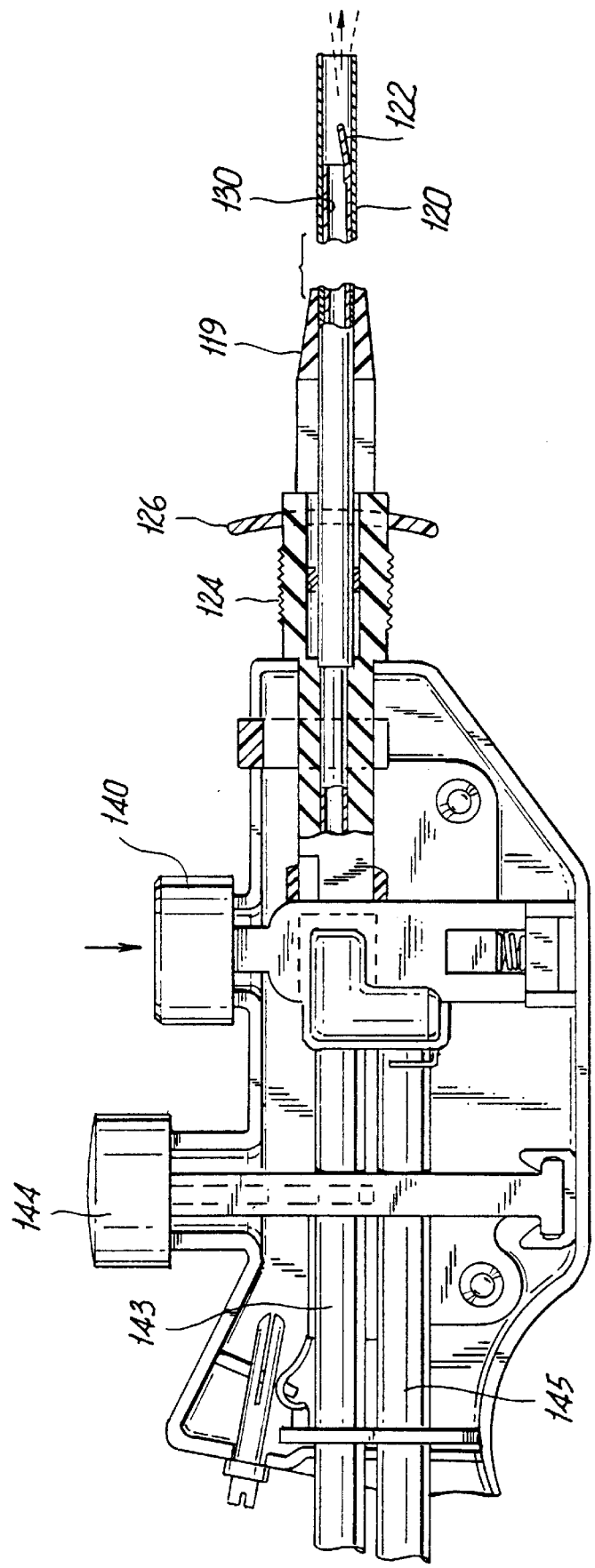
FIG. 17 illustrates a side cut-away plan view of the instrument of FIG. 16 with the slidable sleeve in an extended position.
Figure 20:
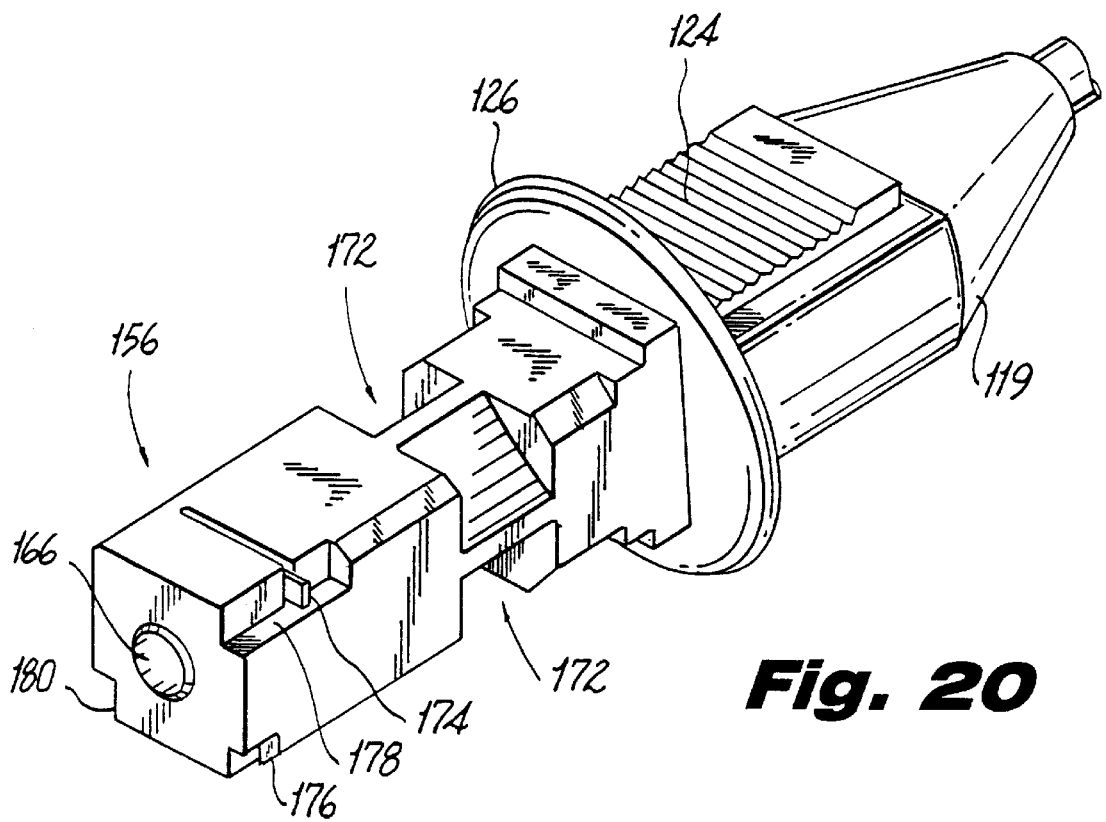

FIGS. 14 and 15 also illustrate the novel connection for the detachable cannula assembly 116. In the embodiment of FIGS. 14 and 15, the detachably secured cannula means for communicating the fluid source and the suction source to the surgical site is the cannula tube 130 and coupling member 156. Coupling member 156 is detachably secured in cannula port 158 through the provision of a locking arrangement which includes release button 128 which is biased into an engaged position by release spring 160. As best seen in FIG. 20, the coupling member 156 is provided with locking notches 172 for engagement with release button 128 as seen in FIG. 19 for securing coupling member 156 within port 158. In order to ensure electrical conductivity to the cannula, electrical contacts 173 and 174 are provided in coupling member 156 within cutout portions 180 and 178, respectively, for engaging leaf springs 151a and 151b disposed in cannula port 158, as described hereinabove. The arrangement of locking notches 172, electrical contacts 173 (FIG. 14) and 174 as well as leaf springs 151a and 151b allow cannula coupling member 156 to be inserted into cannula port 158 as illustrated in FIGS. 13a, 16 and 17, and also to be rotated 90° (FIG. 13b), 180° or 270° (not shown) from the position illustrated in FIGS. 13a, 16 and 17 and then inserted into cannula port 158, while still providing proper alignment of lumen 166 with lumen 167 of handle 112 as well as maintaining electrical contact from bayonet adapter 134 to tool member 122, as described hereinabove. This arrangement allows the surgeon to insert the cannula assembly 116 in any of the above four positions for selectively orientating the working tool 122 with respect to the handle 112.

Figure 21:
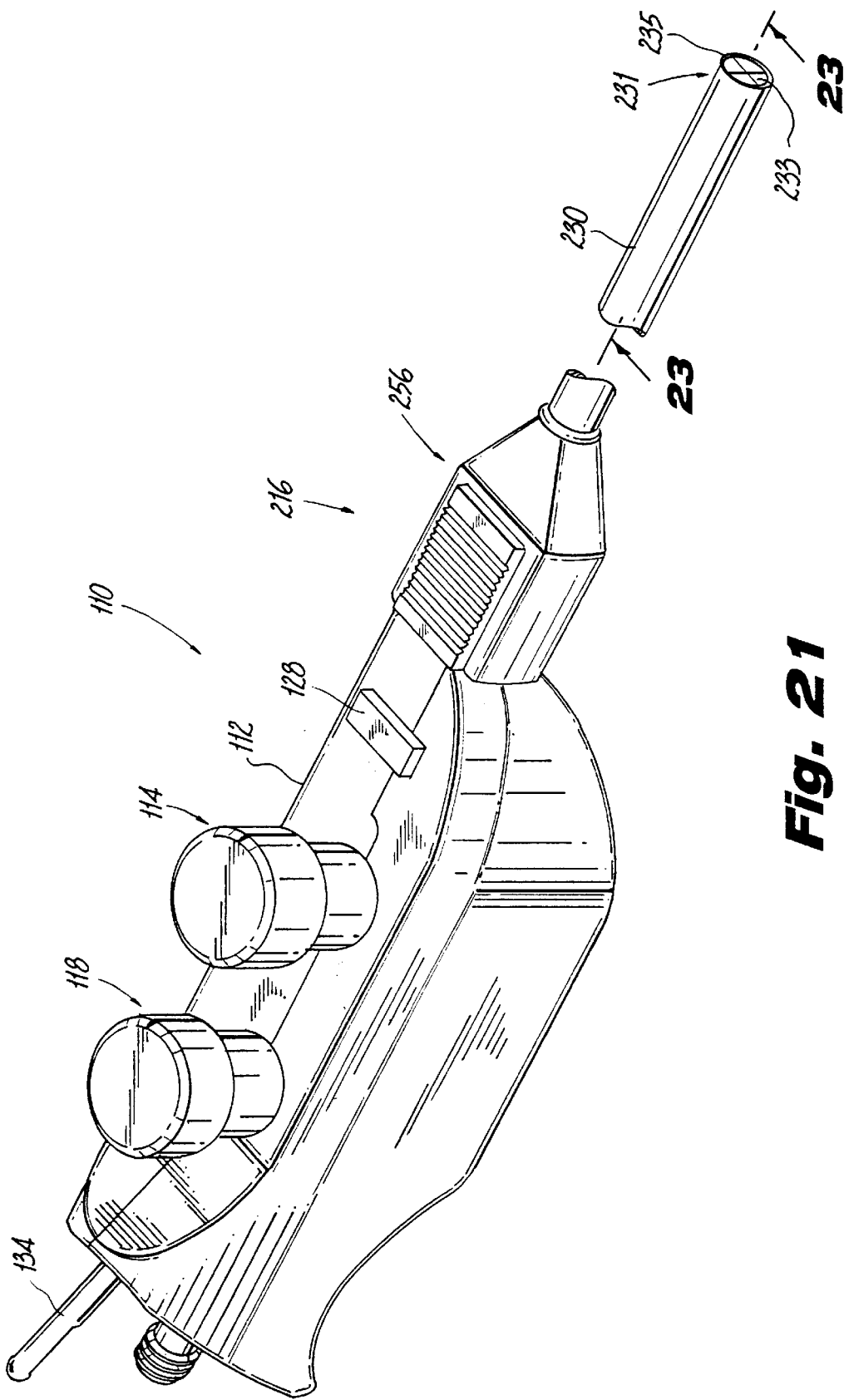
FIG. 21 illustrates a perspective view of the instrument of FIG. 13a utilizing an alternate detachable cannula and coupling mechanism.
Figure 22:
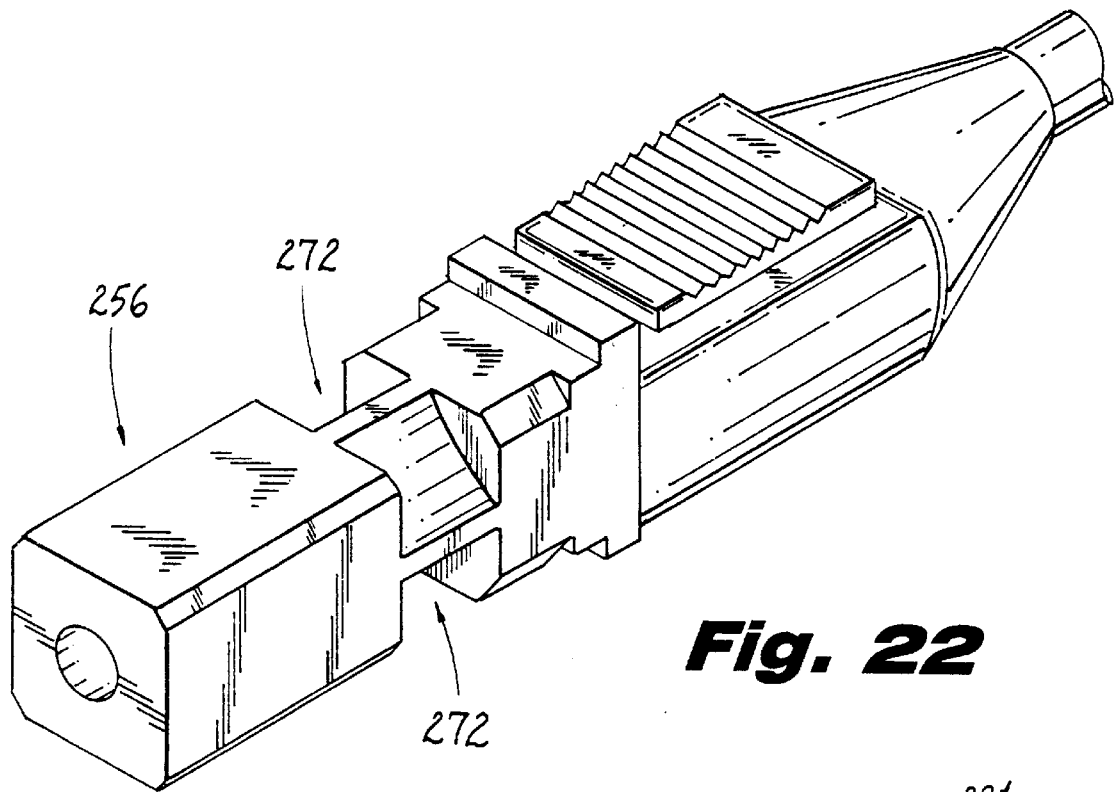
FIG. 22 illustrates an enlarged perspective view of the detachable cannula of FIG. 21.
Figure 23:
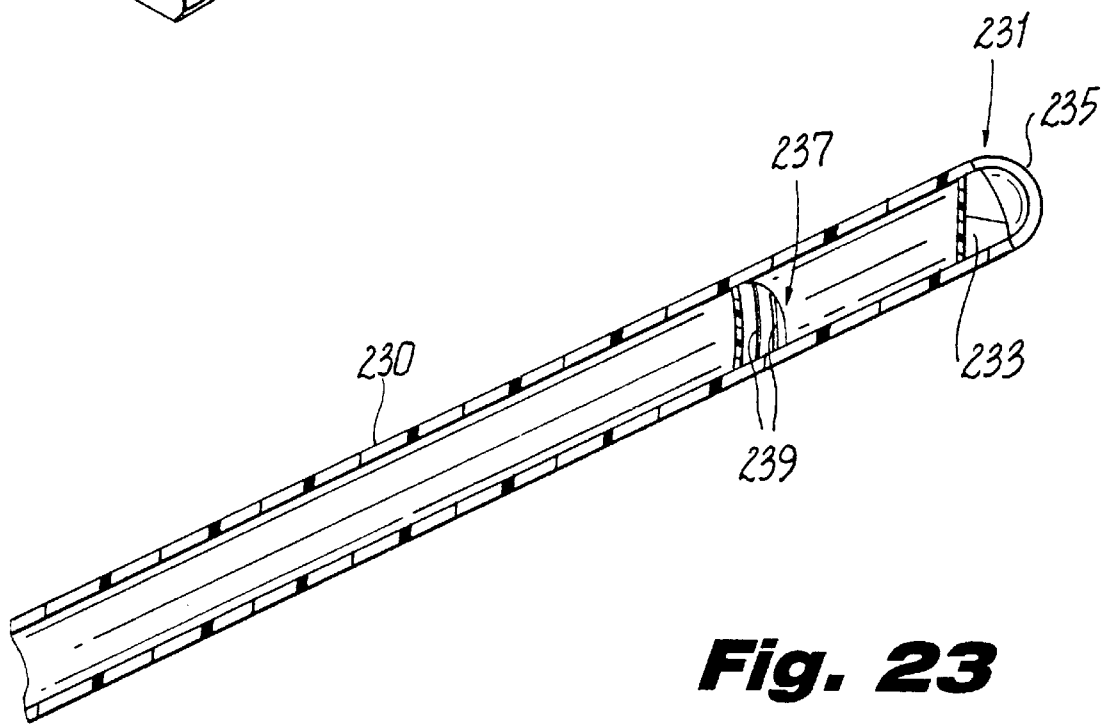
FIG. 23 illustrates a cross-sectional view of the cannula of instrument 21 taken along lines 23—23 showing the filter and valve of the cannula.

Referring now to FIGS. 21–23 there is illustrated an alternate embodiment of the detachable cannula assembly of FIGS. 14 and 15. Detachable cannula assembly 216 includes a cannula coupling member 256 and further includes a cannula 230 extending from cannula coupling member 256. Cannula 230 preferably has a diameter of approximately 10 mm, but may be dimensioned either larger or smaller depending upon the preference of the user and the size of the trocar through which the instrument is to be inserted. Cannula 230 is preferably non-conductive and includes a distal end 231 having a valve 233 disposed therein. Valve 233 is preferably a slit valve mounted to cannula 230 by cap member 235 and preferably allows generally solid material, for e.g. blood clots and gallstones, to enter cannula 230, but prevents the same material from exiting cannula 230. As seen in FIG. 23 cannula 230 further includes a filter 237 disposed therein. Filter 237 has a slotted construction for allowing the fluid source and the suction source to communicate to the surgical site through cannula 230, while preventing the material which has entered the cannula 230 through valve 233 from traveling through cannula 230 and into handle 112 of instrument 110, thereby preventing clogging of the instrument. Filter 237 includes a plurality of slots 239 which are generally hemispherical in shape and is preferably formed integrally with cannula 230, but alternatively may be mounted to cannula 230 by a suitable adhesive. In the embodiment of FIGS. 21–23, the detachably secured cannula means for communicating the fluid source and the suction source to the surgical site is the cannula tube 230 and coupling member 256. Coupling member 256 is detachably secured in cannula port 158 through the provision of a locking arrangement similar to the locking arrangement described hereinabove, which includes release button 128 which is biased into the engaged position by release spring 160. Coupling member 256 differs from coupling member 156, described hereinabove, in that coupling member 256 is preferably not provided with electrical contacts for electro-cautery. As best seen in FIG. 22, the coupling member 256 is provided with locking notches 272 for engagement with release button 128 in order to detachably secure coupling member 256 within port 158.

Turning now to FIGS. 16 and 17, there is illustrated the sliding sleeve 120 in the retracted position as shown in FIG. 16 and in the extended position as shown in FIG. 17. In order to protect the patient during insertion of the cannula through an incision, and further to protect the working tool 122 from damage during the insertion process, cannula body portion 119 slides forward to move the slidable cannula sleeve 120 to the position shown in FIG. 17 where the working tool member 122 is fully protected within the sleeve. In this position, apertures 132 as shown in FIG. 13a, are free to assist in the suction process to clear the surgical site from fluids and small pieces of tissue. Irrigation may also be accomplished in this position without the working tool 122 deflecting the flow of fluid out from the distal end of the cannula.

In order to perform electrocauterization, the working tool 122 is exposed by sliding the sleeve 120 in a proximal direction to the position shown in FIG. 16. This exposes the tool 122, and electrocauterization may be performed upon connection of bayonet adapter 134 to an electrical source. The current is carried through leaf spring 148 to bus bar 150, and then through leaf springs 151a and 151b. Leaf springs 151a and 151b project into cannula port 158, preferably in two places, in order to ensure contact with electrical contact 173 or 174 regardless of the position of cannula 130 when it is inserted into port 158, as described hereinabove. Cannula tube 130 is then energized and conducts the current to working tool 122.

Figure 24:
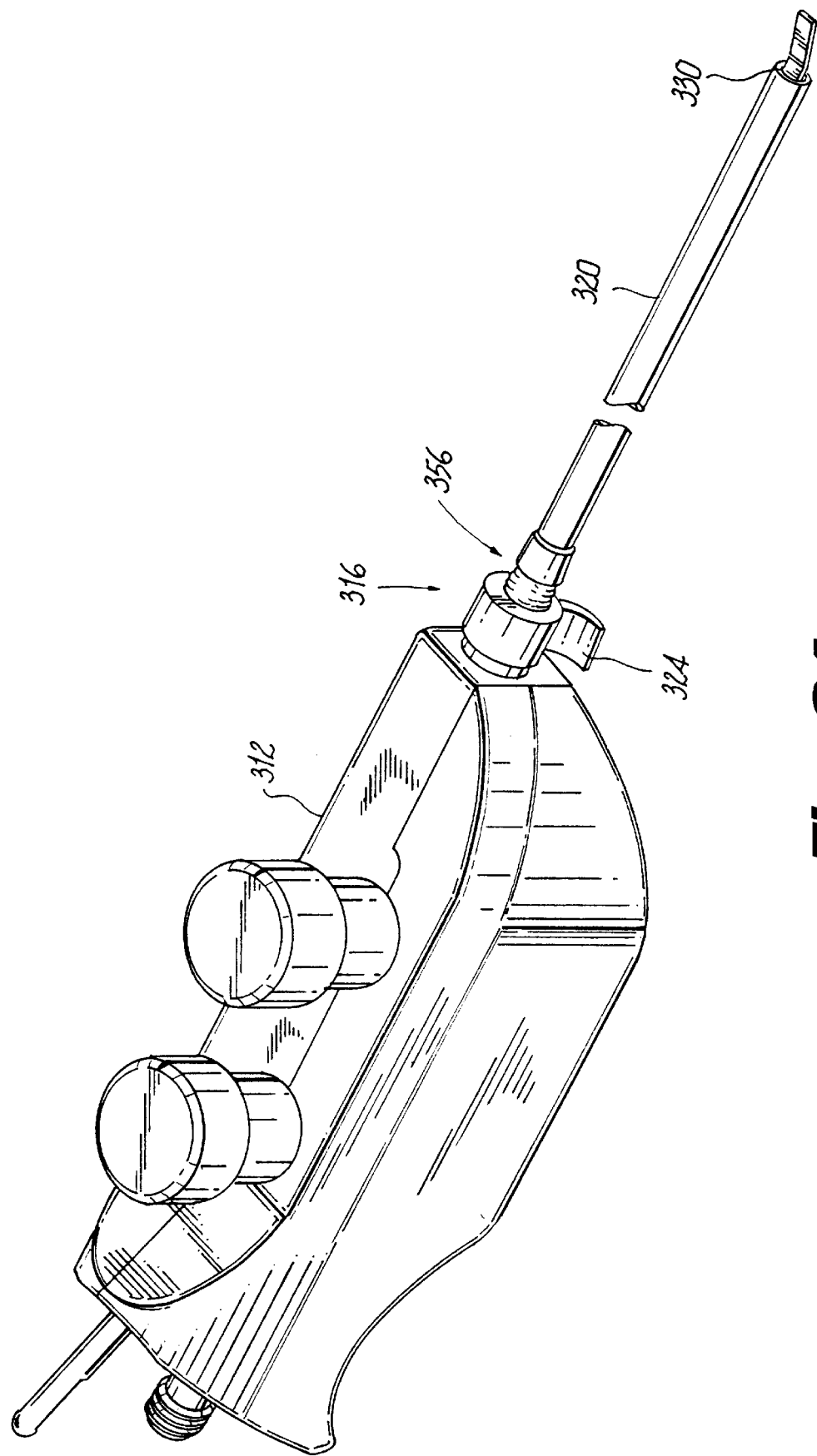
FIG. 24 illustrates a perspective view of the instrument of FIG. 13a utilizing an alternate detachable cannula and coupling mechanism.
Figure 25:
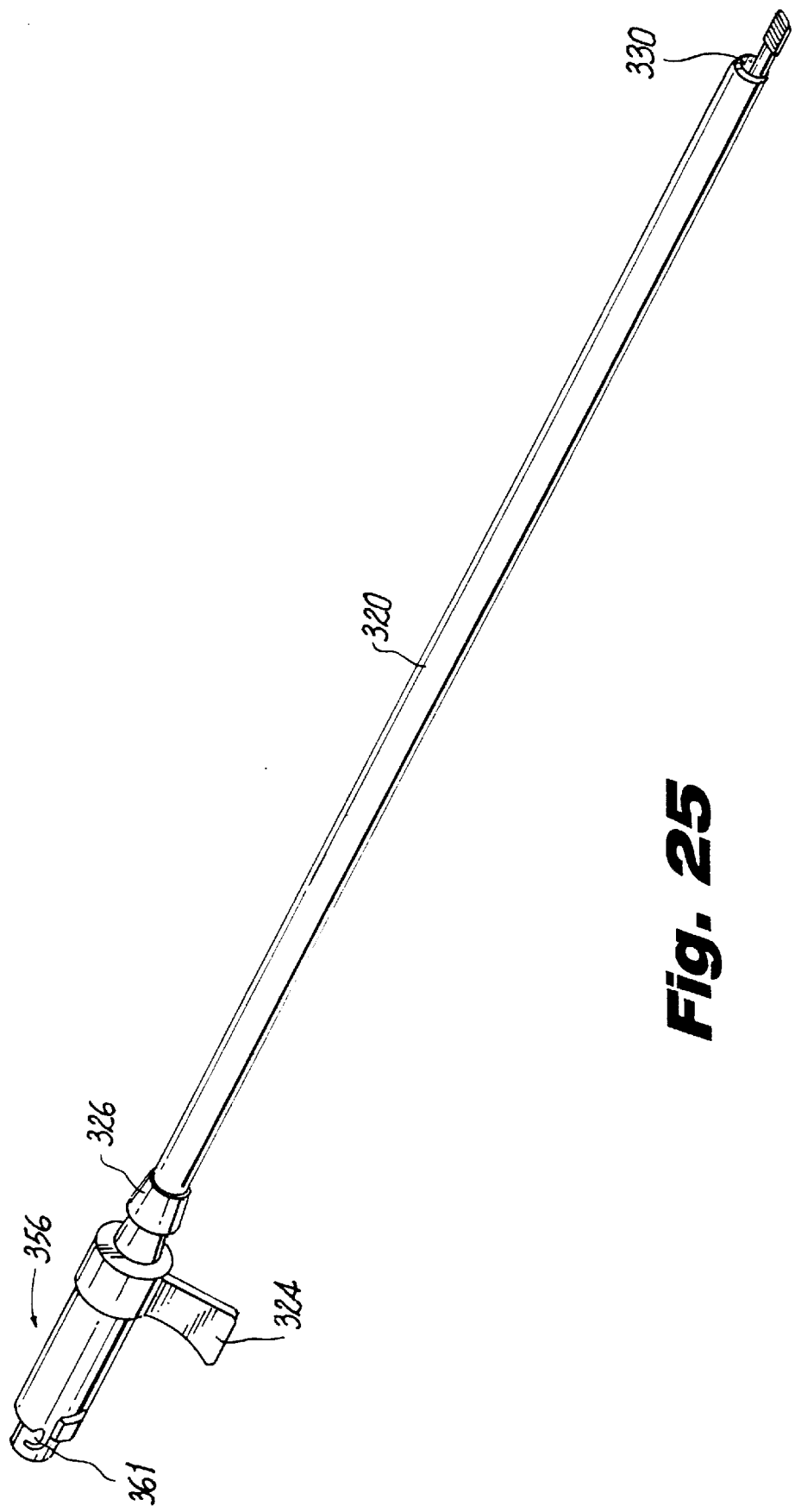
FIG. 25 illustrates an enlarged perspective view of the detachable cannula of FIG. 24.
Figure 26A:
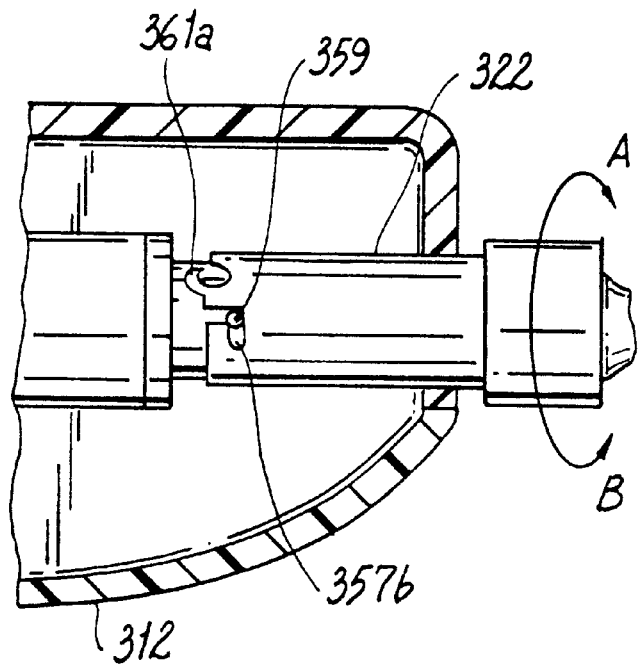
FIGS. 26a and 26b illustrate a partial side plan view in partial cross section of the embodiment of FIG. 24.
Figure 26B:
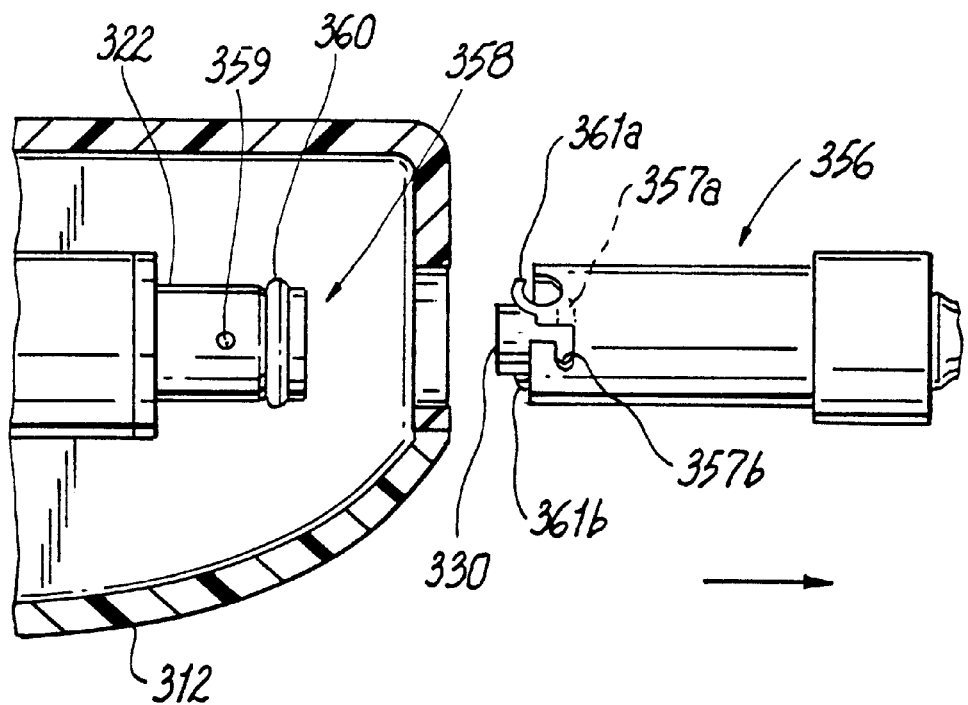

Referring now to FIG. 24, there is illustrated another alternate embodiment of the detachable cannula assembly of FIGS. 14 and 15. Detachable cannula assembly 316 includes a cannula coupling member 356 and preferably further includes a cannula sleeve 320 which is slidably positioned over cannula tube 330. To facilitate movement of cannula sleeve 320 over cannula tube 330, a collar 326 is provided. A grip portion 324 is also provided extending from cannula coupling member 356 in order to facilitate insertion and removal of the cannula assembly 316 within handle portion 312. As best seen in FIGS. 25–26b, in order to detachably secure cannula tube 330 within cannula port 358 a bayonet-type fitting is provided. The bayonet fitting also secures cannula coupling member 356 to port coupling member 322. The connective fitting preferably includes a pair of J-shaped engagement slots 357a and 357b disposed within cannula coupling member 356 which are designed to engage a pair of corresponding posts 359 extending from port coupling member 322. Posts 359 are preferably affixed to port coupling member 322 by a suitable adhesive, but may also be formed integrally therewith, or may be received within a hole formed therein.

Cannula tube 330 is preferably conductive, so as to provide electrocautery capabilities to the instrument, as described hereinabove. A seal, such as O-ring 360, is preferably provided at the distal end of port coupling member 322 to provide a seal between port coupling member 322 and cannula coupling member 356 in order to prevent leakage of gas and/or fluid through the instrument. A pair of living hinges 361a, 361b may also be provided at the proximal end of cannula coupling member 356. Living hinges 361a, 361b are preferably formed integrally with cannula coupling member 356 and act to bias the cannula coupling member 356 against the port coupling member 322. To insert detachable cannula assembly 316 within handle portion 312, posts 359 are aligned with the opening of their corresponding engagement slots 357a and 357b. The cannula coupling member 356 is then inserted over port coupling member 322 such that posts 359 slide into engagement slots 357a and 357b. Cannula coupling member 356 is then rotated in the direction of arrow A in order to secure the posts 359 within their corresponding engagement slots 357a and 357b. In this position cannula tube 330 is secured within cannula port 358. To remove cannula tube 330 from cannula port 358, the opposite procedure is followed, i.e. the cannula coupling member 356 is rotated in the direction of arrow B and then removed from handle portion 312.

Referring once again to FIG. 15, valve mechanism 114 includes first valve actuator 140 which controls first connection port 142 through valve duct 168, while second valve actuator 144 of valve mechanism 118 controls second connection port 146 in a manner similar to that described above. In the embodiment of FIG. 15, the connection means for connecting the device to at least one of a fluid and suction source is first connection port 142 or second connection port 146. Valve mechanisms 118 and 114 include valve bodies 154a and 154b, respectively, which includes the novel valve of the present application which will be described below.

Figure 27:
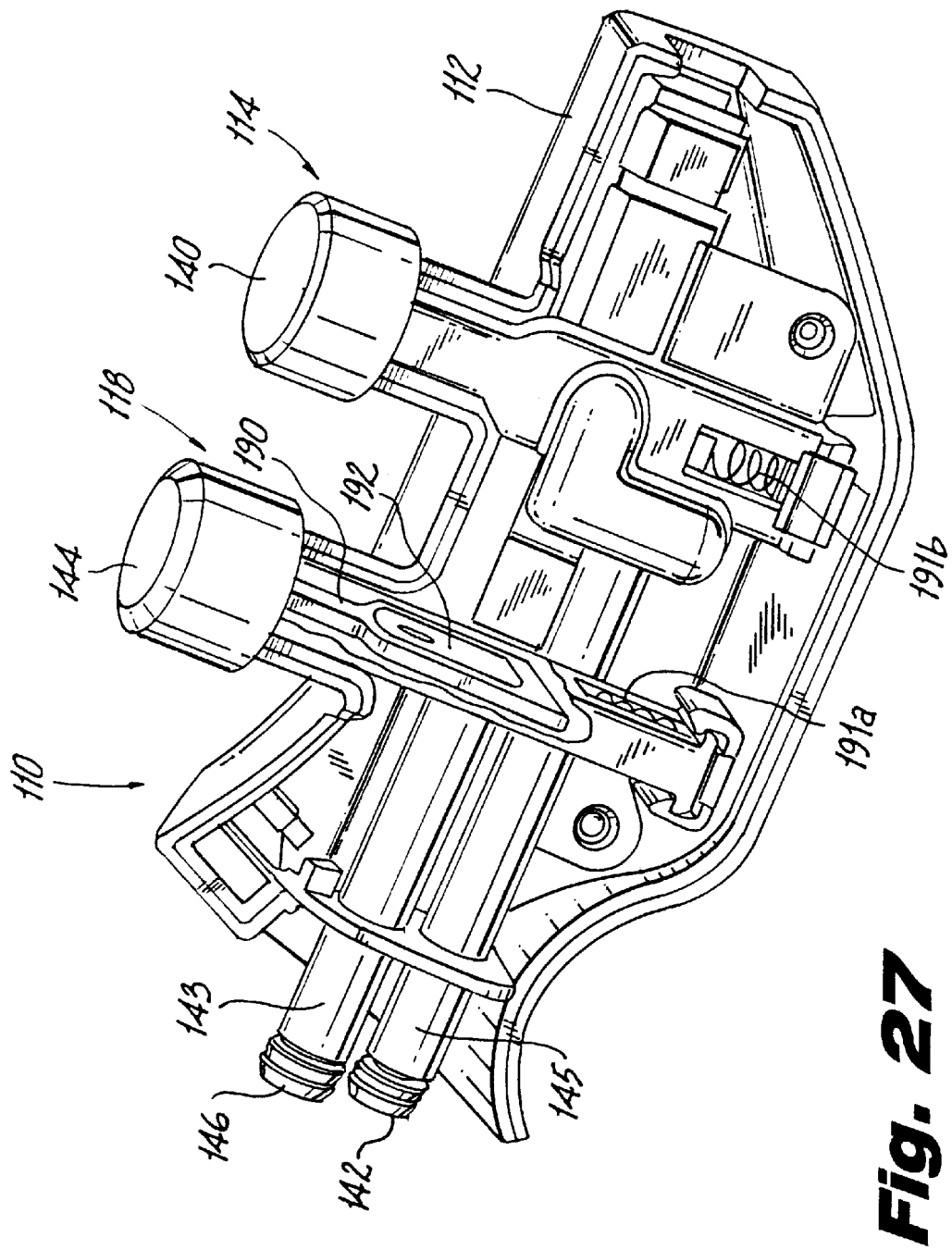
FIG. 27 illustrates a simplified side cut-away perspective view of the handle of the instrument of FIG. 13a, including a partial cut-away view of one of the valves utilized by the instrument.
Figure 28:
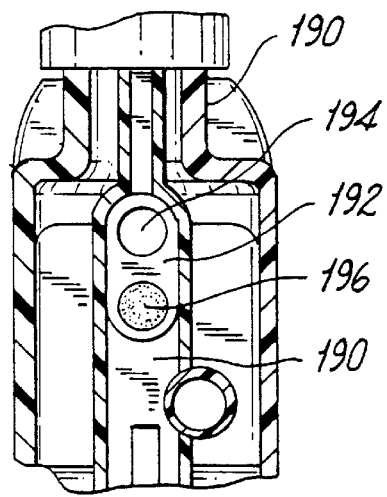
FIG. 28 illustrates a cross-sectional view of the handle of the instrument of FIG. 13a taken along lines 28—28 showing the valve gasket and valve stem of the instrument.

Turning now to FIG. 27, there is illustrated a cutaway view of the handle mechanism of the present application utilizing the novel valve assembly for accommodating higher pressures during a surgical procedure. As described above, the instrument 110 includes a handle portion 112 including a pair of valve mechanisms 114, 118. Instrument 110 is similar to instrument 10 discussed above, except for the provision of the novel valve mechanism for accommodating higher pressures and the novel coupling mechanism for mounting cannula assembly 116. Because valve mechanism 114 and 118 operate in a similar manner, the following description will be in terms of valve mechanism 118 only. It will be appreciated, however, that this description is applicable to valve mechanism 114 as well. Valve mechanism 118 includes an actuator button 144 which operates the sealing mechanism by moving the valve stem 190 against the biasing force of a spring member 191a to move the valve 192 into and out of communication with conduit 143. Conduit 143 provides a passageway through the instrument from the connection port 146 to provide for connection to a source of pressure. Conduit 143 communicates the source of pressure, through the valve mechanism 118, to the cannula 130 similar to that described above. Likewise, conduit 145 communicates a source of pressure through valve mechanism 114 to cannula 130.

As seen in FIGS. 28 and 29a–29c, valve stem 190 includes an opening which accommodates valve 192. Valve 192 includes an aperture 194 and a membrane portion 196. Aperture 194, when moved into communication with conduit 143, provides an opening through valve mechanism 118 so that the source of pressure may be communicated to the surgical site through the cannula 130. Typically, aperture 194 communicates with the conduit when actuator button 144 is depressed, although its position may obviously be reversed. When the actuator button 144 is released, and the valve mechanism 114 is at rest, membrane portion 196 is positioned in the passageway to occlude conduit 143 to prevent the source of fluid pressure from reaching the surgical site through the cannula 130. Valve 192 may be secured in the opening in the valve stem in any known manner, but is preferably captured in valve body 154a and valve stem 190. Valve 192 is preferably oriented in the position shown in FIG. 27, for a source of irrigation in order to prevent leakage, i.e. so that raised walls 198 and 200 face the source side of the handle of the instrument for operation as described below with respect to FIGS. 33a and 33b. For a source of suction, the orientation of the valve is preferably reversed, i.e., the raised walls 198 and 200 face away from the source side of the handle 112. Valve 192 is constructed of a flexible material, preferably a flexible elastomeric material such as Santoprene, manufactured by Monsanto. However, many flexible elastomeric materials may be utilized, to provide the sealing function required of the valve mechanism.

Figure 29A:
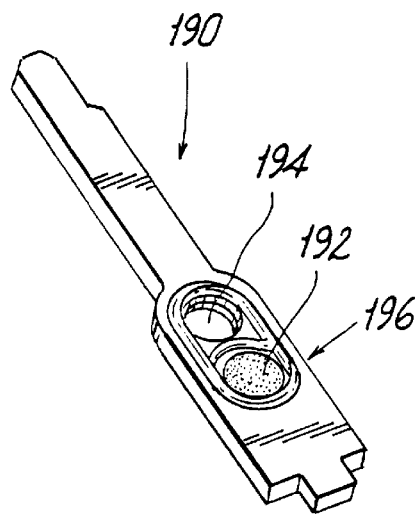
FIGS. 29a–29c illustrate the valve stem and valve of the valve mechanism of FIG. 28, in perspective, bottom elevation, and cross-section along lines 29c—29c, respectively.
Figure 29B:
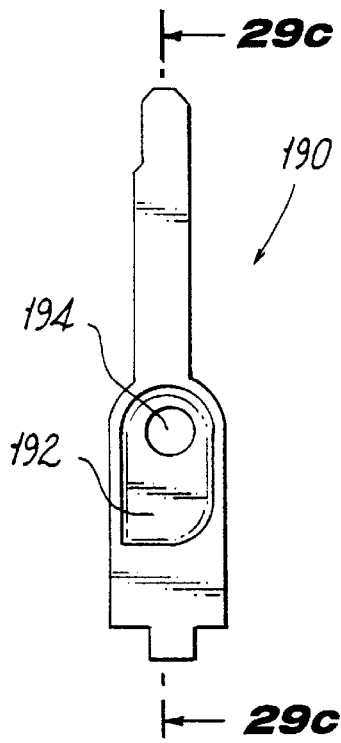
Figure 29C:
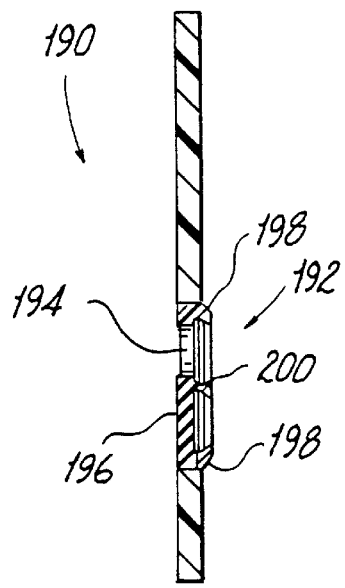
Figure 30A:
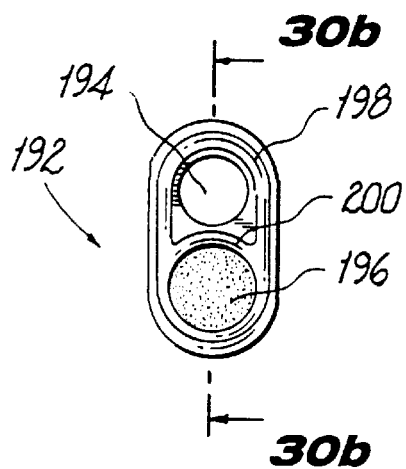
FIGS. 30a–30b illustrate the valve of the present application, in top elevation and cross-section taken along lines 30b—30b, respectively.
Figure 30B:
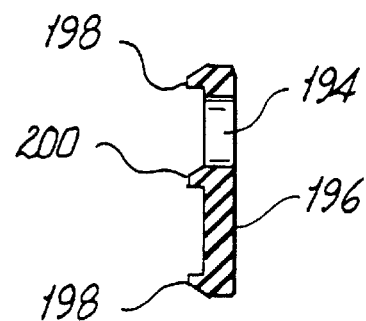

As seen in FIG. 29c and FIGS. 30a and 30b, valve 192 includes raised wall 198 about the perimeter of valve 192, whose function will be described below. In addition, membrane portion 196 is bounded by a similar raised wall 200, and in the preferred embodiment, valve 192 has the oval shape shown in FIG. 30a. The membrane portion 196 preferably has a circular shape for communication with the conduit 143, which also has a circular cross-section, and which is slightly less in diameter than the raised circular wall of the membrane portion 196. As such, the raised walls 198 and 200 have a ramped configuration as seen in FIG. 30b, which provides an overall frustoconical shape to the valve 192, and in particular to the raised wall 200 about the membrane portion 196.

Figure 31:
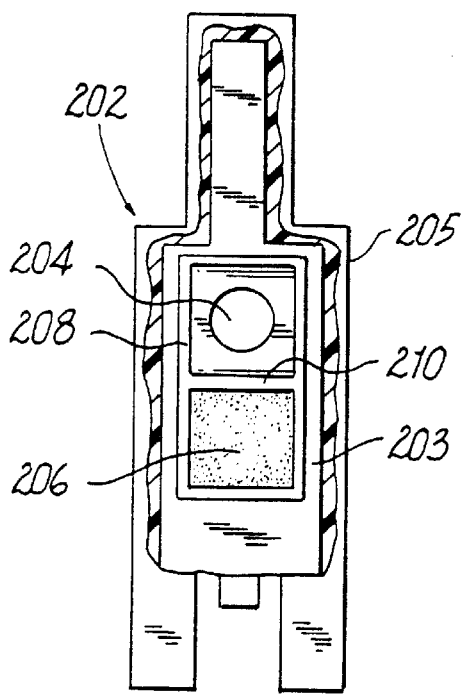
FIG. 31 illustrates a prior art valve, in top elevation and partially cut-away.
Figure 32A:
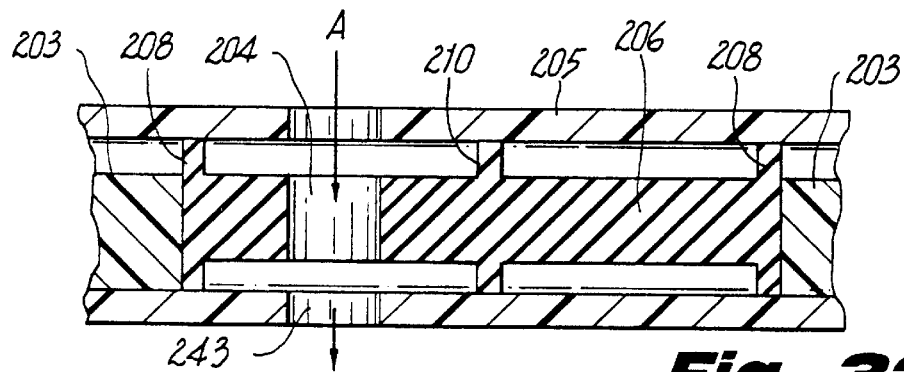
FIGS. 32a–32b illustrate an enlarged, sectional view of the prior art valve of FIG. 31, at rest and under pressure, respectively.
Figure 32B:
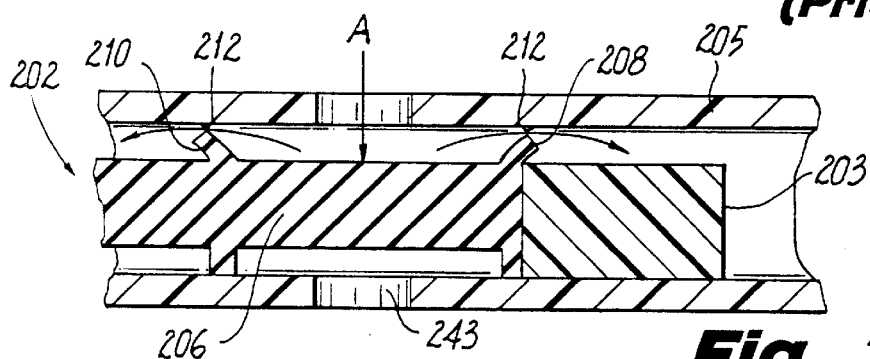

A valve stem 203 containing a prior art valve 202 is illustrated in FIGS. 31 and 32a–32b. Valve stem 203 and valve 202 are disposed within valve body 205. Valve 202 is generally rectangular and includes an aperture 204 and a membrane portion 206, which generally has a square shape and seals the passageway by providing a membrane portion 206 with a greater dimension than the diameter of conduit 243. Valve 202 is provided with a perimeter wall 208 which is slightly raised in relation to membrane portion 206, and membrane portion 206 is separated from aperture 204 by a bisecting wall 210.

Turning now to FIGS. 32–33, the sealing operation of the prior art valve 202 and the valve 192 of the present application will now be described. As seen in FIG. 32a, the prior art valve 202 is in an at-rest position in the opening of valve stem 203, within valve body 205. When a fluid pressure is applied to the valve in the direction of arrow A, such as when the valve stem is in the position shown in FIG. 32b so that the membrane portion 206 occludes the conduit 243, the valve 202 will flex under the pressure applied in the direction of arrow A as shown in FIG. 32b. The flexing of valve 202 causes a gap 212 to exist between the valve body 205 and the raised walls 208, 210. This weakens the valve mechanism, and will not accommodate pressures exceeding the range of 20–30 psi without resulting in some leakage.

Figure 33A:
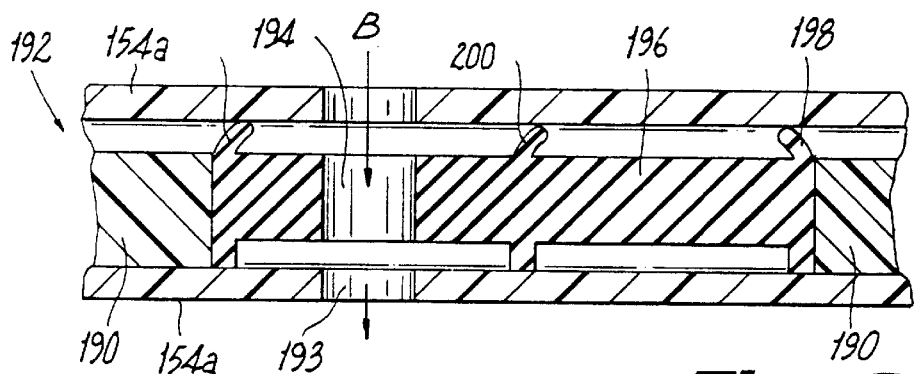
FIGS. 33a–33b illustrate an enlarged, sectional view of the valve of the present application of FIG. 29a–c, at rest and under pressure, respectively.
Figure 33B:
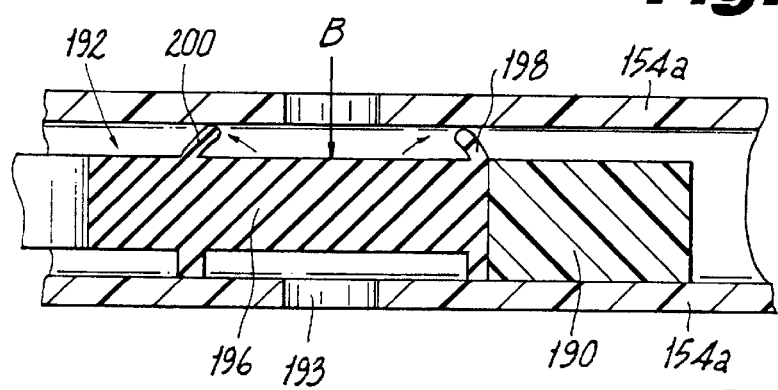

Turning now to FIGS. 33a and 33b, the valve 192, having the frustoconical shape with raised, ramped walls 198 and 200, is shown in FIG. 33a in the at-rest position without the application of fluid pressure. In FIG. 33b, as fluid pressure is applied in the direction of arrow B, it is deflected by membrane portion 196 which flexes under the applied pressure, but due to the raised, ramped walls 198 and 200, the sealing contact point 216 is maintained as ramped walls 198 and 200 are pressed harder against valve body 154a by the pressure. This occurs because as the valve 192 flexes the outer surface of the walls 198 and 200 continue to contact valve body 154a due to their raised, ramped design. As seen in FIG. 33b, the ramped walls 198 and 200 are able to maintain contact with valve body thereby preventing the formation of a gap, as compared with gap 212 seen with the prior art valve 202 in FIG. 32b. The novel valve accommodates higher static pressure, typically within the range of 65–75 psi, preferably 70 psi.

Figure 34:
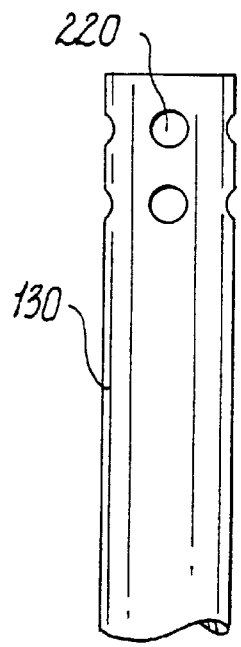
FIG. 34 illustrates the distal end of the cannula of the instrument of the present application.

The use of the novel valve 192 as described herein allows for use of the surgical aspirating and irrigating instrument at higher pressures to increase the suction capabilities and the irrigation capabilities of the instrument, since it is of course contemplated that both valve mechanisms 114 and 118 incorporate the valve 192 and valve stem 190 described in the present application. Related to this, the cannula 130 may include a plurality of holes 220 at the distal end of the cannula as seen in FIG. 34. Preferably, a series of four rows of holes are provided, separated by 90°. This increases the surface area of the holes for suction purposes, and the cannula may be used in conjunction with the sleeve 26 illustrated in FIGS. 1 and 2 above to provide the hydrodissection function. Preferably, however, it is desirable to provide the holes 132 on the sliding cannula sleeve 120 as shown and described above with respect to FIGS. 13a, 16 and 17.

In use, the instrument of the present application provides a variably orientable aspiration and irrigation device which may also be used for dissecting tissue. Interchangeable or replaceable cannulas, each of which may include a different working tip for performing a variety of surgical functions, are provided for use with the instrument. Furthermore, an insertion port for reception of a surgical instrument is provided in aligned communication with the single lumen cannula which communicates the surgical instrument to the surgical site. In addition, a surgical instrument locking device and a bayonet connection member for electro-cautery procedures may also be provided.

It will be understood that various modifications may be made to the embodiments disclosed herein. For example, although it is contemplated that the novel valve as described above will be incorporated into both valve mechanisms, it may be incorporated only into one valve mechanism, i.e., irrigation only. In addition, although the detachable cannula assembly, the novel valve, instrument insertion port and electrocautery have been described as incorporated into a single instrument, any combination of these features is possible. Therefore, the above description should not be construed as limiting, but merely as exemplifications of preferred embodiments. Those skilled in the art will envision other modifications within the scope and spirit of the claims appended hereto.

What is claimed is:

1. A surgical instrument comprising:
   a) a handle portion;
   b) a cannula member definig a lumen, the cannula member extending distally from the handle portion;
   c) a first connection port adapted to communicate with a source of irrigation fluid, the first connection port being in fluid communication with the lumern of the cannula member;
   d) a second connection port adapted to communicate with a vacuum source, the second connection port being in fluid communication with the lumen of the cannula member; and
   e) a surgical blow tube positioned within the lumen of the cannula member,
   wherein tie cannula member is positionable adjacent a surgical site to selectively transport irrigation fluid thereto, aspirate the surgical site, and transport pressurized gas thereto.

2. A surgical instrument according to claim 1, further comprising a first valve mechanism supported by the handle portion positioned between the first connection port and the lumen of the cannula member, the first valve mechanism being selectively actuable to communicate the lumen of the cannula member with a source of irrigation fluid.

3. A surgical instrument according to claim 2, further comprising a second valve mechanism supported by the handle portion positioned between the second connection port and the lumen of the cannula member, the second valve mechanism being selectively actuable to provide aspiration within the lumen of the cannula member.

4. A surgical instrument according to claim 1, further comprising an insertion port formed in the handle portion, the insertion port communicating with the lumen of the cannula member, wherein the insertion port is axially aligned with the lumen of the cannula member.

5. A surgical instrument according to claim 4, wherein the surgical blow tube is inserted through the lumen of the cannula member via the insertion port.

6. A surgical instrument according to claim 5, further comprising a seal supported adjacent the insertion port, the seal being dimensioned to sealingly engage the surgical blow tube.

7. A surgical instrument according to claim 6, wherein the seal is an elastomeric seal.

8. A surgical instrument according to claim 5, further comprising a valve mechanism positioned on a proximal end of the surgical blow tube.

9. A surgical instrument according to claim 1, further comprising an extension adapter configured to be received within the first connection port, the extension adapter being adapted to communicate with a source of irrigation fluid.

10. A surgical instrument according to claim 1, further comprising a tool member supported at the distal end of the cannula member.

11. A surgical instrument according to claim 10, wherein the tool member is in the form of a spatula tip adapted to dissect, manipulate and/or cauterize tissue.

12. A surgical instrument according to claim 11, wherein the spatula tip has rounded edges.

13. A surgical instrument comprising:
   a) a handle portion;
   b) a cannula member extending distally from the handle portion;
   c) a first connection port supported by the handle portion and communicating with the cannula member, the first connection port being adapted to communicate with a source of irrigation fluid;
   d) a second connection port supported by the handle portion and communicating with the cannula member, the second connection port being adapted to communicate with a vacuum source;
   e) an insertion port supported by the handle portion and being axially aligned with the cannula member; and
   f) a blow tube removably positioned within the cannula member via the insertion port and having an adapter configured to engage a source of pressurized gas.

14. A surgical instrument according to claim 13, further comprising a first valve mechanism supported by the handle portion positioned between the first connection port and the cannula member, the first valve mechanism being selectively actuable to communicate the cannula member with a source of irrigation fluid.

15. A surgical instrument according to claim 14, further comprising a second valve mechanism supported by the handle portion positioned between the second connection port and the cannula member, the second valve mechanism being selectively actuable to provide aspiration within the cannula member.

16. A surgical instrument according to claim 15, further comprising a seal positioned adjacent the insertion port, the seal being dimensioned to sealingly engage the blow tube.

17. A surgical instrument according to claim 16, further comprising a valve mechanism positioned on a proximal end of the blow tube.

18. A surgical instrument according to claim 17, further comprising an extension adapter configured to be received within the first connection port, the extension adapter being adapted to communicate with a source of irrigation fluid.

19. A surgical instrument according to claim 18, further comprising a tool member supported at the distal end of the cannula member.

20. A surgical instrument according to claim 19, wherein the tool member is in the form of a spatula tip adapted to dissect, manipulate and/or cauterize tissue.

* * * * *